United States Patent [19]

Gaster et al.

[11] Patent Number: 4,504,480

[45] Date of Patent: Mar. 12, 1985

[54] PENTACYCLIC COMPOUNDS

[75] Inventors: Laramie M. Gaster, Bishop's Stortford; Barry S. Orlek, London, both of England

[73] Assignee: Beecham Group p.l.c., Brentford, England

[21] Appl. No.: 472,218

[22] Filed: Mar. 4, 1983

[30] Foreign Application Priority Data

Mar. 5, 1982 [GB] United Kingdom ............... 8206558

[51] Int. Cl.³ ................... A61K 31/495; C07D 223/14
[52] U.S. Cl. ............................. 514/214; 260/239 BD; 260/239 D; 260/243.3; 260/245.5
[58] Field of Search ...................... 260/243.3; 424/250

[56] References Cited

U.S. PATENT DOCUMENTS

| | | | |
|---|---|---|---|
| 4,316,900 | 2/1982 | Wasley | 424/250 |
| 4,469,697 | 9/1984 | Gardner et al. | 260/243.3 |

FOREIGN PATENT DOCUMENTS

| | | |
|---|---|---|
| 055546 | 7/1982 | European Pat. Off. |
| 2257203 | 5/1973 | Fed. Rep. of Germany |
| 2505239 | 8/1975 | Fed. Rep. of Germany |
| 1173783 | 12/1969 | United Kingdom |
| 1229252 | 4/1971 | United Kingdom |
| 1229253 | 4/1971 | United Kingdom |

OTHER PUBLICATIONS

Gaster, Chem. Abst. vol. 100, 1984, 34571k, eq. EP 88575.
K. Kubo et al., "Studies on N-cyclohexylanthranilic acid analogs. I. Synthesis and analgesic activity", *Chemical Abstracts*, 88, No. 23, p. 570, col. 2, Abstract No. 169910z, (Jun. 5, 1978).
S. Veeraraghaven et al., "Reissert Compound Studies XLII. Synthesis and Reactions of the 3,4-dihydro-beta-carboline Reissert Compound and Observations on alpha, beta and gamma-carbolines", *Chemical Abstracts*, 95, No. 25, p. 506, col. 2, Abstract No. 21993t, (Dec. 21, 1981) (J. Heterocycl. Chem. vol. 18, No. 5, pp. 909–915).
B. Walker and P. Wrobel, "Stereospecific cis Radical Addition, Convincing Evidence for a 1,3-Radial Transfer Reaction," *J.C.S. Chem. Comm.*, 1980, pp. 462–463.
S. Ogren et al., "Reevaluation of the Indoleamine Hypothesis of Depression, Evidence for a Reduction of Functional Activity of Central 5-HT Systems by Antidepressant Drugs," *J. Neural. Trans.*, 46, pp. 85–103 (1979).
L. Stein et al., "Effects of Benzodiazepines on Central Serotonergic Mechanisms," *Advances in Biochemical Psychopharmacology*, vol. 14, pp. 29–44 (Raven Press, New York City 1975).
Maggi et al., "Differential Effects of Antidepressant Treatment on Brain Monoaminergic Receptors," *Eur. J. Pharm.* 61, pp. 91–98 (1980).

*Primary Examiner*—Donald G. Daus
*Assistant Examiner*—Cecilia Shen
*Attorney, Agent, or Firm*—James F. Haley, Jr.; Charles B. Smith

[57] ABSTRACT

Compounds of formula (I),

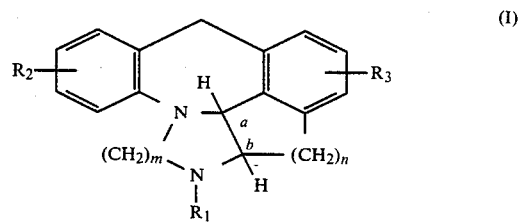

or an N-oxide or pharmaceutically acceptable salt thereof, wherein $R_1$ is hydrogen, $C_{1-7}$ alkyl, $C_{3-7}$ cycloalkyl, $C_{4-7}$ cycloalkenyl or $C_{1-4}$ alkyl substituted by $C_{2-7}$ alkenyl, $C_{2-7}$ alkynyl, $C_{3-7}$ cycloalkyl, hydroxy, thiol, $C_{1-4}$ alkoxy, $C_{1-4}$ alkylthio, carboxy, $C_{1-4}$ alkoxycarbonyl, $C_{1-4}$ alkanoyl, amino optionally substituted by one or two $C_{1-4}$ alkyl or by $C_{4-6}$ polymethylene optionally containing an oxygen or nitrogen atom, aminocarbonyl optionally N-substituted by one or two $C_{1-4}$ alkyl, or benzoyl or phenyl either being optionally ring-substituted by $C_{1-4}$ alkyl, $C_{1-4}$ alkoxy, halogen or trifluoromethyl, $R_2$ and $R_3$ are the same or different and are hydrogen, hydroxy, $C_{1-4}$ alkyl, $C_{1-4}$ alkoxy, $C_{1-4}$ alklthio, halogen or trifluoromethyl, m is 1 to 3 and n is 1 or 2, the hydrogen atom bonded to the $C_a$ carbon atom being trans to the hydrogen atom bonded to the $C_b$ carbon atom, having mood-modifying activity such as anti-depressant activity.

12 Claims, No Drawings

PENTACYCLIC COMPOUNDS

This invention relates to novel pentacyclic compounds having pharmacological activity, to processes and intermediates of use in their preparation, to pharmaceutical compositions containing them, and to their use in the treatment of mammals.

U.K. Pat. No. 1,173,783 discloses compounds of formula (A);

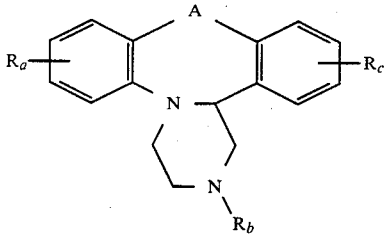

wherein $R_a$ and $R_c$ each represent a hydrogen or halogen atom, a hydroxy, lower acyloxy, alkyl or alkoxy group, or a trifluoromethyl group, $R_b$ represents hydrogen, a lower alkyl or aralkyl group, an aminoethyl or aminopropyl group N-substituted by one or more lower alkyl groups, or a lower alkyl group forming a substituent of an N-containing heterocyclic ring, the said ring being directly bonded to the nitrogen atom of the piperazine ring, and A represents a single bond, or a methylene, ethylene or —CH=CH— group.

U.K. Pat. No. 1,229,252 discloses compounds of formula (B);

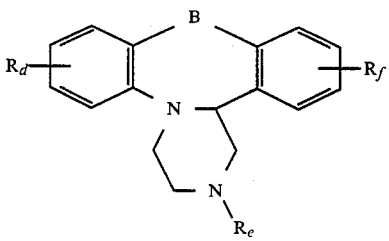

wherein $R_d$ and $R_f$ represent hydrogen, halogen, hydroxy, acyloxy, lower alkoxy or lower alkyl or trifluoromethyl, $R_e$ represents hydrogen, lower alkyl, lower aralkyl, aminoethyl or aminopropyl optionally N-substituted by lower alkyl, or lower alkyl substituted by a nitrogen-containing heterocyclic ring, and B represents oxygen, sulphur, or NRg, Rg representing lower alkyl.

The compounds of formulae (A) and (B) are disclosed as having anti-inflammatory, anti-serotoninic, anti-histaminic, anti-phlogistic and cardiovascular activities. In addition, the compound of formula (A), wherein $R_a$ and $R_c$ are both hydrogen, $R_b$ is methyl and A is methylene, is commonly known as mianserin and is marketed as an anti-depressant agent for the treatment of depression in mammals.

U.K. Pat. No. 1,229,253 discloses componds of formula (C);

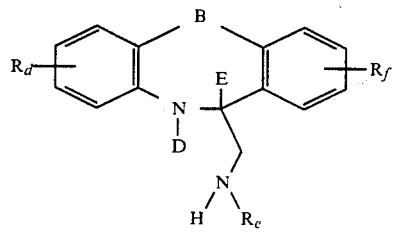

wherein $R_d$, $R_e$, $R_f$ and B are as defined in relation to formula (B) above, and D and E are either hydrogen or together represent a double bond between the nitrogen and carbon atoms to which they are attached, and functional derivatives thereof. Such compounds are disclosed as having sedative, tranquilising and anti-depressant activity.

U.S. Pat. No. 4,316,900 discloses compounds of formula (D);

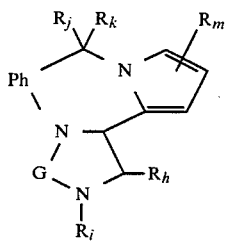

and salts thereof derived from pharmaceutically acceptable acids or ammonium or alkali metal bases, wherein $R_h$, $R_j$ and $R_k$ are each hydrogen or lower alkyl, $R_l$ is hydrogen, lower or higher alkyl, lower alkenyl, lower alkynyl, $C_{3-7}$ cycloalkyl, cycloalkenyl or lower alkyl substituted by cycloalkyl, hydroxy, amino, mono- or di-lower alkylamino, carboxy, lower carbalkoxy, carbamoyl, mono- or di-lower alkyl carbamoyl, phenyl, lower alkanoyl or benzoyl, Ph is 1,2-phenylene unsubstituted or substituted by up to two members selected from lower alkyl, lower alkoxy, lower akkylthio, halogen and trifluoromethyl, G is lower alkylene separating both nitrogen atoms by 2 or 3 carbon atoms and $R_m$ is hydrogen, lower alkyl, carboxy, lower carbalkoxy or lower alkyl substituted by hydroxy, amino, mono- or di-lower alkylamino, and the lower alkoxycarbonyl, lower or higher alkanoyl, admantoyl, carbamoyl, mono- or di-lower alkylcarbamoyl, $C_{3-7}$ cycloalkylcarbonyl or benzoyl derivatives thereof, and the 2-N-oxide, 2-lower alkyl or 2-phenyl lower alkyl quaternaries and salts thereof derived from pharmaceutically acceptable acids or bases. Such compounds are described as antidepressant agents suitable, for example, in the treatment or management of mental depression in mammals.

A structurally distinct class of compounds has now been discovered which compounds are dibenz[b,e]azepines in which the azepine nitrogen atom and the azepine carbon atom adjacent thereto are joined with $C_{1-3}$ alkyleneaminomethylene to form a 5- to 7-membered ring, characterized by a methylene or ethylene bridge from the carbon atom of the aminomethylene moiety to the carbon atom of the benzo moiety that is in the ortho-position to the azepine ring and that is on the same side as, and three carbon's distance from, the azepine nitrogen atom, the bridge thus forming a 5- or 6-membered ring. Such compounds, moreover, have been found to have pharmacological activity, in particular mood-modifying activity, such as anti-depressant activity.

Accordingly, the present invention provides a compound of formula (I);

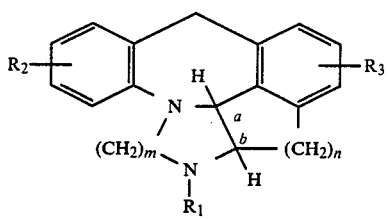

(I)

or an N-oxide or pharmaceutically acceptable salt thereof, wherein $R_1$ is hydrogen, $C_{1-7}$ alkyl, $C_{3-7}$ cycloakyl, $C_{4-7}$ cycloalkenyl or $C_{1-4}$ alkyl substituted by $C_{2-7}$ alkenyl, $C_{2-7}$ alkynyl, $C_{3-7}$ cycloalkyl, hydroxy, thiol, $C_{1-4}$ alkoxy, $C_{1-4}$ alkylthio, carboxy, $C_{1-4}$ alkoxycarbonyl, $C_{1-4}$ alkanoyl, amino optionally substituted by one or two $C_{1-4}$ alkyl or by $C_{4-6}$ polymethylene optionally containing an oxygen or nitrogen atom, aminocarbonyl optionally N-substituted by one or two $C_{1-4}$ alkyl, or benzoyl or phenyl either being optionally ring-substituted by $C_{1-4}$ alkyl, $C_{1-4}$ alkoxy, halogen or trifluoromethyl, $R_2$ and $R_3$ are the same or different and are hydrogen, hydroxy, $C_{1-4}$ alkyl, $C_{1-4}$ alkoxy, $C_{1-4}$ alkylthio, halogen or trifluoromethyl, m is 1 to 3 and n is 1 or 2, the hydrogen atom bonded to the $C_a$ carbon atom being trans to the hydrogen atom bonded to the $C_b$ carbon atom.

Within the definition for $R_1$ is a sub-group, wherein $R_1$ is hydrogen, $C_{1-4}$ alkyl, $C_{1-4}$ alkyl substituted by amino optionally substituted by one or two $C_{1-4}$ alkyl or by $C_{4-6}$ polymethylene optionally containing an oxygen or nitrogen atom, or $C_{1-4}$ alkyl substituted by phenyl optionally substituted by $C_{1-4}$ alkyl, $C_{1-4}$ alkoxy, halogen or trifluoromethyl.

When $R_1$ is $C_{1-4}$ alkyl substituted by phenyl optionally substituted as hereinbefore defined, examples of such optional substituents include methyl, ethyl, methoxy, ethoxy, fluoro, chloro, bromo or trifluoromethyl. Preferably, phenyl is unsubstituted.

When $R_1$ is $C_{1-4}$ alkyl substituted by amino optionally substituted as hereinbefore defined, examples of such optional substituents include methyl and ethyl and, together with the nitrogen atom, piperidino and morpholino.

Preferably, $R_1$ is hydrogen or $C_{1-4}$ alkyl, in particular $C_{1-4}$ alkyl, such as methyl and ethyl.

Within the definition for $R_2$ and $R_3$ is a sub-group, wherein $R_2$ and $R_3$ are the same or different and are hydrogen, $C_{1-4}$ alkyl, $C_{1-4}$ alkoxy, halogen or trifluoromethyl.

Preferred examples for $R_2$ and $R_3$ are hydrogen, hydroxy, methyl, ethyl, methoxy, ethoxy, bromo, chloro, fluoro and trifluoromethyl. Preferably, $R_2$ is hydrogen, methoxy, hydroxy, methyl or chloro and $R_3$ is hydrogen.

Preferably, m is 1 or 2.

Preferably, n is 1.

The compounds of the invention have chiral centres at the $C_a$ and $C_b$ carbon atoms and therefore can exist in enantiomeric forms. The present invention extends to such enantiomers individually and as mixtures including racemates.

Particularly preferred compounds within formula (I) are the compounds of the examples described hereinafter or an N-oxide or pharmaceutically acceptable salt thereof. The most preferred compound of formula (I) is trans-12-methyl-1,10,11,12,12a, 12b-hexahydro-5H-9b,12-diazabenzo[5,6]cyclohepta[1,2,3,4-def]fluorene, which is the compound prepared in Example 1, or an N-oxide or pharmaceutically acceptable salt thereof.

An N-oxide of a compound of formula (I) includes the oxide of either nitrogen atom shown in formula (I) and the oxide of any nitrogen-containing substitutent for $R_1$.

A pharmaceutically acceptable salt of a compound of formula (I) includes an acid addition salt of either nitrogen atom shown in formula (I) and of any nitrogen-containing substituent for $R_1$, the acid addition salt being derived from a pharmaceutically acceptable inorganic or organic acid, such as hydrochloric acid, hydrobromic acid, sulphuric acid, maleic acid and acetic acid. A pharmaceutically acceptable salt of a compound of formula (I) also includes alkali metal or alkaline earth metal salts of any carboxy-containing substitutent for $R_1$. Examples of such salts include potassium, sodium, calcium and magnesium salts.

The present invention also provides a process for preparing a compound of formula (I), as defined hereinbefore, which comprises cyclising a compound of formula (II);

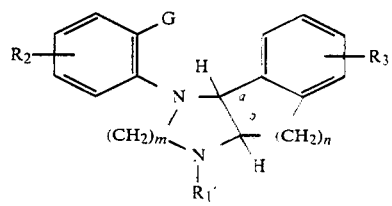

(I)

wherein $R_2$, $R_3$, m, n and the configuration of the $C_a$ and $C_b$ hydrogen atoms are as defined hereinbefore, $R_1'$ is $R_1$ or $C_{1-4}$ alkoxycarbonyl, phenoxycarbonyl or benzyloxycarbonyl and G is formyl, carboxy or a $C_{1-4}$ alkyl ester thereof or is $CH_2L_1$, $L_1$ being a leaving group; in the case when $R_1'$ is $C_{1-4}$ alkoxycarbonyl, phenoxycarbonyl or benzyloxycarbonyl, converting $R_1'$ into $R_1$; in the case when G is formyl, carboxyl or a $C_{1-4}$ alkyl ester thereof, reducing the resulting carbonyl or hydroxymethylene moiety to a methylene moiety; optionally converting $R_1$, $R_2$ or $R_3$ in the resulting compound of formula (I) into another $R_1$, $R_2$ or $R_3$; and optionally forming an N-oxide or pharmaceutically acceptable salt thereof.

Preferred examples of the leaving group ($L_1$) include hydroxy, bromo, chloro, $C_{1-4}$ alkoxy, $C_{1-4}$ alkanoyloxy, $C_{1-4}$ alkoxycarbonyloxy, tosyloxy and mesyloxy.

When the leaving group ($L_1$) is hydroxy, $C_{1-4}$ alkoxy, $C_{1-4}$ alkanoyloxy, $C_{1-4}$ alkoxycarbonyloxy, tosyloxy or mesyloxy, or when G is formyl, carboxy or a $C_{1-4}$ alkyl ester thereof, the cyclisation reaction is preferably carried out in the presence of a dehydrating agent, for example orthophosphoric acid or methane sulphonic acid contining phosphorus pentoxide.

When the leaving group ($L_1$) is bromo or chloro, the cyclisation reaction is preferably carried out in the presence of a Lewis acid, such as aluminum trichloride.

When $R_1'$ is $C_{1-4}$ alkoxycarbonyl, phenoxycarbonyl or benzyloxycarbonyl, the process proceeds through an intermediate of formula (III);

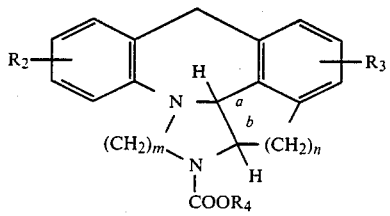

(III)

wherein $R_2$, $R_3$, m, n and the configuration of the $C_a$ and $C_b$ hydrogen atoms are as defined hereinbefore and $R_4$ is $C_{1-4}$ alkyl, phenyl or benzyl.

The conversion of the $C_{1-4}$ alkoxycarbonyl, phenoxycarbonyl or benzyloxycarbonyl group into $R_1$ may be carried out in accordance with any appropriate known procedure. For example, the group may be hydrolysed with concomitant decarboxylation using ethanolic sodium hydroxide to give a compound of formula (I), wherein $R_1$ is hydrogen, which may then optionally be converted into another $R_1$, as described hereinafter. Alternatively, the group may be reduced using, for example, lithium aluminium hydride in a solvent, for example, ether or tetrahydrofuran, to give a compound of formula (I), wherein $R_1$ is methyl.

When G is formyl, carboxy or a $C_{1-4}$ alkyl ester thereof, the process proceeds through an intermediate of formula (IV);

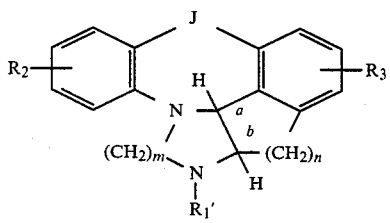

(IV)

wherein $R_1'$, $R_2$, $R_3$, m, n, and the configuration of the $C_a$ and $C_b$ hydrogen atoms are as defined hereinbefore and J is CO or CHOH, when G in formula (II) is carboxy or a $C_{1-4}$ alkyl ester thereof, or is CHOH, when G in formula (II) is formyl.

The reduction of the resulting carbonyl or hydroxymethylene moiety may be carried out using, for example, catalytic hydrogenation.

Examples of an optional conversion of $R_1$ in a compound of formula (I) into another $R_1$ include the conversion of $C_{1-4}$ alkyl substituted by hydroxy into $C_{1-4}$ alkyl substituted by thiol by, for example, first forming a $C_{1-4}$ alkyl halide, such as the chloride, and then reacting the $C_{1-4}$ alkyl halide with potassium hydrogen sulphide, or into $C_{1-4}$ alkyl substituted by $C_{1-4}$ alkoxy using, for example, sodium hydride and a $C_{1-4}$ alkyl halide; the conversion of $C_{1-4}$ alkyl substituted by thiol into $C_{1-4}$ alkyl substituted by $C_{1-4}$ alkylthio using, for example, a base and a $C_{1-4}$ alkyl halide; the conversion of $C_{1-4}$ alkyl substituted by $C_{1-4}$ alkoxycarbonyl into $C_{1-4}$ alkyl substituted by carboxy by hydrolysis; the conversion of $C_{1-4}$ alkyl substituted by carboxy into $C_{1-4}$ alkyl substituted by aminocarbonyl optionally N-substituted by one or two $C_{1-4}$ alkyl by, for example, first forming the carboxylic acid halide, such as the chloride, and then reacting the acid halide with ammonia optionally substituted by one or two $C_{1-4}$ alkyl; and the conversion of $C_{1-3}$ alkyl substituted by aminocarbonyl optionally N-substituted by one or two $C_{1-4}$ alkyl into $C_{1-4}$ alkyl substituted by amino optionally substituted by one or two $C_{1-4}$ alkyl by reduction.

An important sub-class of an optional conversion of $R_1$ is that in which a compound of formula (I), wherein $R_1$ is hydrogen, is converted into another compound of formula (I), wherein $R_1$ is as follows:

(a) wherein $R_1$ is $C_{1-7}$ alkyl, by alkylation with a $C_{1-7}$ alkyl halide in a solvent, such as acetone, in the presence of a base, or by reductive $C_{1-7}$ alkylation in which a mixture of a compound of formula (I), wherein $R_1$ is hydrogen, and a $C_{1-7}$ aldehyde is reduced catalytically or with sodium cyanoborohydride in a solvent, such as ethanol, or by $C_{2-7}$ acylation using a carboxylic acid chloride or anhydride in a solvent, such as methylene dichloride, in the presence of an organic or inorganic base, for example pyridine, triethylamine or potassium carbonate, and then reduction of the $C_{2-7}$ acylated derivative with, for example, lithium aluminium hydride;

(b) wherein $R_1$ is $C_{3-7}$ cycloalkyl, by reductive alkylation, as described in paragraph (a), using a $C_{3-7}$ cycloalkanone;

(c) wherein $R_1$ is $C_{3-7}$ cycloalkenyl, by reaction with a $C_{3-7}$ cycloalkenyl halide, such as a $C_{3-7}$ cycloalkenyl bromide, when the halide atom is allylic, or by reductive alkylation, as described in paragraph (a), using a $C_{3-7}$ cycloalkenone;

(d) wherein $R_1$ is $C_{1-4}$ alkyl substituted by $C_{2-7}$ alkenyl or $C_{2-7}$ alkynyl, by reaction with a $C_{2-11}$ alkenyl or $C_{2-11}$ alkynyl halide, such as a $C_{2-11}$ alkenyl or $C_{2-11}$ alkynyl bromide, in a solvent, such as acetone, in the presence of a base, such as potassium carbonate;

(e) wherein $R_1$ is $C_{1-4}$ alkyl substituted by $C_{3-7}$ cycloalkyl, by acylation with a compound of formula (V);

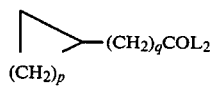

(V)

in which p is 1 to 5, q is 0 to 3 and $L_2$ is a leaving group, such as chloro, and then reduction of the acylated derivative, as described in paragraph (a);

(f) wherein $R_1$ is $C_{1-4}$ alkyl substituted by hydroxy, by reaction with aqueous formaldehyde when $R_1$ is hydroxymethyl, by reaction with ethylene oxide when $R_1$ is hydroxyethyl, or by Michael addition with ethyl acrylate or by reaction with ethyl w-bromobutyrate and reduction of the ester with lithium aluminium hydride when $R_1$ is respectively hydroxypropyl or hydroxybutyl;

(g) wherein $R_1$ is $C_{1-4}$ alkyl substituted by $C_{1-4}$ alkoxycarbonyl, by reaction with a compound of formula (VI);

$$L_3-(CH_2)_r-CO_2R_5 \qquad (VI)$$

in which $R_5$ is $C_{1-4}$ alkyl, $L_3$ is a leaving group, such as bromo, and r is 1 to 4, in a solvent, such as methylene dichloride, in the presence of a base, or by Michael addition with a $C_{1-4}$ alkyl acrylate when $R_1$ is ethyl substituted by $C_{1-4}$ alkoxycarbonyl;

(h) wherein $R_1$ is $C_{1-4}$ alkyl substituted by $C_{1-4}$ alkanoyl, by reaction with a $C_{1-4}$ alkanoyl $C_{1-4}$ alkyl halide or by Michael addition with a $C_{1-4}$ alkyl vinyl ketone when $R_1$ is ethyl substituted by $C_{1-4}$ alkanoyl;

(i) wherein $R_1$ is $C_{1-4}$ alkyl substituted by amino optionally substituted by one or two $C_{1-4}$ alkyl or by $C_{4-6}$ polymethylene optionally containing an oxygen or nitrogen atom, by reaction with a compound of formula (VII);

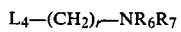

in which $R_6$ and $R_7$ are hydrogen or $C_{1-4}$ alkyl or together are $C_{4-6}$ polymethylene optionally containing an oxygen or nitrogen atom, $L_4$ is a leaving group, such as chloro, and r is as hereinbefore defined, in a solvent, such as acetone, in the presence of a base, or by reaction with bromoacetyl bromide, reaction with $HNR_6R_7$, $R_6$ and $R_7$ being as defined hereinbefore, and then reduction, as described in paragraph (a), when $R_1$ is ethyl substituted by amino optionally substituted by one or two $C_{1-4}$ alkyl or by $C_{4-6}$ polymethylene optionally containing an oxygen or nitrogen atom;

(j) wherein $R_1$ is $C_{1-4}$ alkyl substituted by aminocarbonyl optionally N-substituted by one or two $C_{1-4}$ alkyl, by reaction with a compound of formula (VIII);

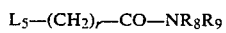

in which $L_5$ is a leaving group, such as halide, in particular bromide, r is as hereinbefore defined and $R_8$ and $R_9$ are hydrogen or $C_{1-4}$ alkyl;

(k) wherein $R_1$ is $C_{1-4}$ alkyl substituted by benzoyl or phenyl either being optionally substituted by $C_{1-4}$ alkyl, $C_{1-4}$ alkoxy, halogen or trifluoromethyl, by reaction with the correspondingly substituted $C_{1-4}$ alkyl halide, such as the bromide.

The present invention extends to all of the above conversions, whether singly or in combination, and to the intermediates used therein, which together are of formula (IX);

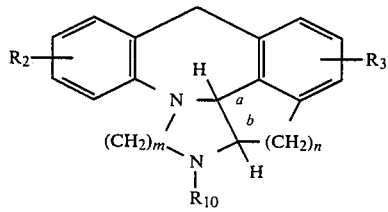

wherein $R_2$, $R_3$, m, n and the configuration of the $C_a$ and $C_b$ hydrogen atoms are as defined hereinbefore and $R_{10}$ is $C_{1-4}$ alkyl substituted by halogen or halocarbonyl or is $C_{1-4}$ alkylcarbonyl, $C_{3-7}$ cycloalkylcarbonyl, $C_{3-7}$ cycloalkyl $C_{1-3}$ alkylcarbonyl or halo $C_{1-4}$ alkylcarbonyl.

When $R_1$ in formula (II) is a functional group that may possibly interfere with the course of the reaction or that may not possibly survive it, then it is preferred to carry out the preparation of a compound of formula (I) with $R_1$ as hydrogen and subsequently to convert the hydrogen atom into the desired group for $R_1$ by, for example, one or more of the conversions described hereinbefore.

An example of an optional conversion of $R_2$ or $R_3$ in a compound of formula (I) into another $R_2$ or $R_3$ is the conversion of $C_{1-4}$ alkoxy into hydroxy using, for example, aqueous hydrobromic acid.

The optional formation of an N-oxide may be carried out by reacting a compound of formula (I) with an organic peracid, such as m-chloroperbenzoic acid.

The optional formation of a pharmaceutically acceptable acid addition salt of a compound of formula (I) may be carried out by simple reaction of a compound of formula (I) with a pharmaceutically acceptable acid.

The optional formation of a pharmaceutically acceptable alkali or alkaline earth metal salt of a compound of formula (I), wherein $R_1$ is a carboxy-containing substituent, may be carried out by reaction of a compound of formula (I) with an alkali or alkaline earth metal or the hydroxide thereof.

The present invention provides a second process for preparing a compound of formula (I), as defined hereinbefore, which comprises reacting a compound of formula (X);

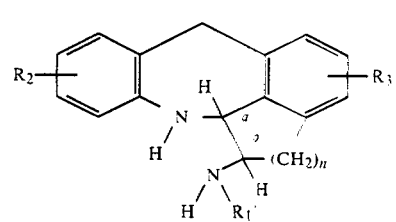

wherein $R_1'$, $R_2$, $R_3$, n and the configuration of the $C_a$ and $C_b$ hydrogen atoms are as defined hereinbefore, with a compound of formula (XI);

wherein $L_7$ and $L_8$ are leaving groups, s and u are 0 or 1 is 0 to 3 such that $s+t+u$ is 1 to 3; in the case when s or u is 1, reducing the carbonyl moiety to give a methylene moiety; in the case when $R_1'$ is $C_{1-4}$ alkoxycarbonyl, phenoxycarbonyl or benzyloxycarbonyl, converting $R_1'$ into $R_1$; optionally converting $R_1$, $R_2$ or $R_3$ in the resulting compound of formula (I) into another $R_1$, $R_2$ or $R_3$; and optionally forming an N-oxide or pharmaceutically acceptable salt thereof.

Preferred examples of the leaving groups ($L_7$ and $L_8$) include halo, such as chloro and bromo, $C_{1-4}$ alkoxy, and labile acyloxy, such as mesyloxy and tosyloxy.

Preferred examples of a compound of formula (XI) including diethyl oxalate, bromoacetyl bromide, methyl bromoacetate, dibromoethane, oxalyl chloride and phosgene. Apart fom diethyl oxalate which is used neat, all these compounds are reacted with a compound of formula (X), when $R_1'$ is other than $C_{1-4}$ alkoxycarbonyl, phenoxycarbonyl or benzyloxycarbonyl, in a solvent, for example, benzene, toluene, methylene dichloride, dimethyl sulphoxide or diethyl ether, in the presence of an organic or inorganic base, for example triethylamine, pyriding, picoline or potassium carbonate. On the other hand, when $R_1'$ is $C_{1-4}$ alkoxycarbonyl, phenoxycarbonyl or benzyloxycarbonyl, the reaction at the carbamate nitrogen requires a solvent, such as dimethylformamide, and the presence of a strong base, such as sodium hydride.

When s or u is 1, the process proceeds through an intermediate of formula (XII);

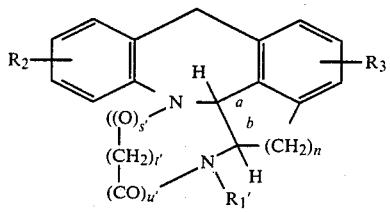

(XII)

wherein $R_1'$, $R_2$, $R_3$, n and the configuration of the $C_a$ and $C_b$ hydrogen atoms are as defined hereinbefore and s', t' and u' respectively are the same as s, t and u, as defined hereinbefore, with the proviso that at least one of s and u is 1.

The reduction of the carbonyl moiety to give a methylene moiety is preferably carried out with diborane or lithium aluminium hydride.

When m in formula (I) is 2 or 3, however, s and u are preferably 0, thus avoiding the need for an additional reduction step.

The conversion of $R_1'$, when $C_{1-4}$ alkoxycarbonyl, phenoxycarbonyl or benzyloxycarbonyl, into $R_1$, the optional conversion of $R_1$, $R_2$ or $R_3$ in the resulting compound of formula (I) into another $R_1$, $R_2$ or $R_3$, and the optional formation of an N-oxide or pharmaceutically acceptable salt may be carried out as described hereinbefore.

The present invention provides a third process for preparing a compound of formula (I), wherein m is 2, which comprises cyclising a compound of formula (XIII);

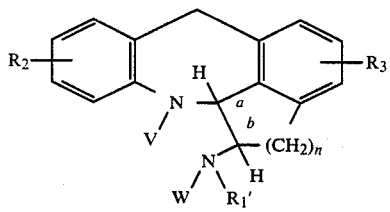

(XIII)

wherein $R_1'$, $R_2$, $R_3$, n and the configuration of the $C_a$ and $C_b$ hydrogen atoms are as defined hereinbefore and one of V and W is hydrogen and the otherr is $(CH_2)_2L_9$, $L_9$ being a leaving group; in the case when $R_1'$ is $C_{1-4}$ alkoxycarbonyl, phenoxycarbonyl or benzyloxycarbonyl, converting $R_1'$ into $R_1$; optionally converting $R_1$, $R_2$ or $R_3$ in the resulting compound of formula (I) into another $R_1$, $R_2$ or $R_3$; and optionally forming an N-oxide or pharmaceutically acceptable salt thereof.

Preferred examples of the leaving group ($L_9$) include halo, such as chloro and bromo, and labile acyloxy, such as mesyloxy and tosyloxy.

The cyclisation may be carried out in a solvent in the presence of a base, as described hereinbefore for the reaction between compounds of formulae (X) and (XI).

The conversion of $R_1'$, when $C_{1-4}$ alkoxycarbonyl phenoxycarbonyl or benzyloxycarbonyl, into $R_1$, the optional conversion of $R_1$, $R_2$ or $R_3$ in the resulting compound of formula (I) into another $R_1$, $R_2$ or $R_3$, and the optional formation of an N-oxide or pharmaceutically acceptable salt may be carried out as described hereinbefore.

The compound of formula (XIII) may be prepared by converting the hydroxy moiety in a compound of formula (XIV);

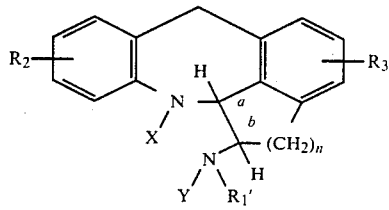

(XIV)

wherein $R_1'$, $R_2$, $R_3$, n and the configuration of the $C_a$ and $C_b$ hydrogen atoms are as defined hereinbefore and one of X and Y is hydrogen and the other is hydroxyethyl, into a leaving group ($L_9$).

In the case of the aforementioned examples for the leaving group ($L_9$), the conversion may be carried out by reacting a compound of formula (XIV) with thionyl chloride, hydrogen bromide, mesyl or tosyl chloride.

The compound of formula (XVI) may in turn be prepared by reacting a compound of formula (X), as hereinbefore defined, with ethylene oxide in a solvent, such as ethanol, at, for example, room temperature. When $R_1'$ is $C_{1-4}$ alkoxycarbonyl, phenoxycarbonyl or benzyloxycarbonyl, the reaction occurs preferentially at the azepine nitrogen atom so that the major resulting compound of formula (XIV) is that wherein X is hydroxyethyl and Y is hydrogen. When, on the other hand, $R_1'$ is $R_1$, the reaction occurs preferentially at the nitrogen atom attached to $R_1$ so that the major resulting compound of formula (XIV) is that wherein X is hydrogen and Y is hydroxyethyl.

The compounds of formulae (II) and (X) can both be prepared from a compound of formula (XV);

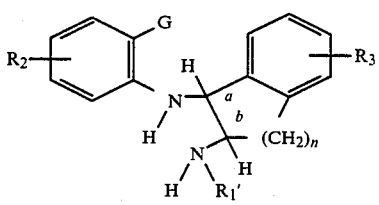

(XV)

wherein $R_1'$, $R_2$, $R_3$, n, G and the configuration of the $C_a$ and $C_b$ hydrogen atoms are as defined hereinbefore; (i) in the case of a compound of formula (II), by reaction with a compound of formula (XI), as defined hereinbefore, and, in the case where s or u is 1, reducing the carbonyl moiety to a methylene moiety; or (ii) in the case of a compound of formula (X), by cyclisation to form the axepine ring.

The reaction between the compounds of formulae (XV) and (XI) to give a compound of formula (II) may be carried out in a similar manner to the reaction between the compounds of formulae (X) and (XI), as described hereinbefore. When either of the leaving groups ($L_7$ and $L_8$) in a compound of formula (XI) is halo and s or u is 1 and when g in formula (XV) is $CH_2L_1$, $L_1$ being hydroxy, there is a risk of a side-reaction between the compound of formula (XI) and the hydroxymethyl substituent in the compound of formula (XV). It is therefore preferred not to use this combination of variables, for example, by using a compound of formula (XI), wherein s and u are 0, or by using another value for the leaving group ($L_7$ or $L_8$) or the leaving group ($L_1$). Alternatively, the hydroxymethyl substituent may be protected using a standard method and then the reaction with a compound of formula (XI) may be carried out and the resulting compound deprotected using a standard method.

When s or u is 1, the preparation proceeds through an intermediate of formula (XVI);

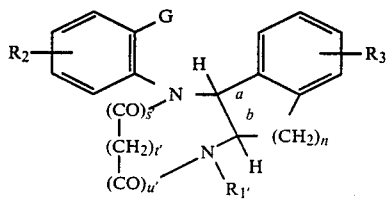

(XVI)

wherein $R_1'$, $R_2$, $R_3$, n, G, the configuration of the $C_a$ and $C_b$ hydrogen atoms, s', t' and u' are as defined hereinbefore.

The reduction of the carbonyl moiety may be carried out in a similar manner to the reduction of the carbonyl moiety in an intermediate of formula (XII) although it is possible that G, when formyl, carboxy or a $C_{1-4}$ alkyl ester thereof, may be reduced as a side-reaction. For such a combination of variables, therefore, it is preferred to use a selective reducing agent that would minimise such side-reaction occurring, such as diborane. Alternatively, as any reduction of formyl, carboxy or a $C_{1-4}$ alkyl ester thereof would result mainly in a hydroxymethyl substituent, it may be desirable to allow the side-reaction to occur especially as hydroxymethyl is a favourable substituent for cyclisation. As a further alternative, the hydroxymethyl substituent may be oxidised back to formyl or carboxy using Manganese dioxide or potassium permanganate and, if a $C_{1-4}$ alkyl ester were required, esterifying the carboxy group so formed.

The cyclisation of a compound of formula (XV) to give a compound of formula (X) may be carried out in a similar manner to the cyclisation of a compound of formula (II).

The compound of formula (XV) may be prepared by reducing a compound of formula (XVII);

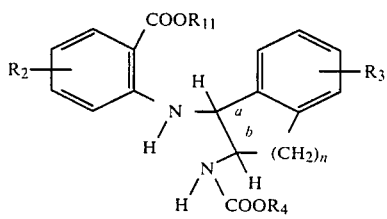

(XVII)

wherein $R_2$ to $R_4$, n and the configuration of the $C_a$ and $C_b$ hydrogen atoms are as defined hereinbefore and $R_{11}$ is $C_{1-4}$ alkyl; optionally converting the hydroxy group of the hydroxymethyl substituent in the resulting compound of formula (XVIII),

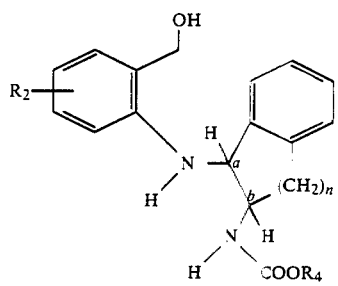

(XVIII)

wherein $R_2$ to $R_4$, n and the configuration of the $C_a$ and $C_b$ hydrogen atoms are as defined hereinbefore, into another leaving group ($L_1$), or optionally oxidising the hydroxymethyl substituent to formyl or carboxy and optionally esterifying a carboxy group so formed into a $C_{1-4}$ alkyl ester thereof; and optionally converting the $C_{1-4}$ alkoxycarbonyl, phenoxycarbonyl or benzyloxycarbonyl group into $R_1$.

In order not to reduce the $C_{1-4}$ alkoxycarbonyl, phenoxycarbonyl or benzyloxycarbonyl group, the reduction of a compound of formula (XVII) is preferably carried out with lithium aluminium hydride at a low temperature or with lithium triethylborohydride.

The optional conversion of the hydroxy group of the hydroxymethyl substituent in the resulting compound of formula (XVIII) may be carried out conventionally. For example, the optional conversion of the hydroxy group into one of the other leaving groups ($L_1$), as defined hereinbefore, may be carried out with thionyl chloride (when $L_1$ is chloro), phosphorous tribromide (when $L_1$ is bromo), a $C_{1-4}$ alcohol and acid (when $L_1$ is $C_{1-4}$ alkoxy), mesyl or tosyl chloride (when $L_1$ is mesyl or tosyl), a $C_{1-4}$ alkanoyl chloride or anhydride (when $L_1$ is $C_{1-4}$ alkanoyloxy) and a $C_{1-4}$ alkoxycarbonyl chloride (when $L_1$ is $C_{1-4}$ alkoxycarbonyloxy).

The optional oxidation of the hydroxymethyl substituent in a compound of formula (XVIII) into formyl, carboxy or a $C_{1-4}$ alkyl ester thereof may be carried out by reaction with manganese dioxide (to give formyl), with potassium permanganate (to give carboxy) or with a mixture of manganese dioxide, sodium cyanide, acetic acid and a $C_{1-4}$ alkanol (to give a $C_{1-4}$ alkyl ester).

It is preferred however that no conversion of the hydroxy group or the hydroxymethyl substituent is carried out and that therefore the leaving group ($L_1$) is hydroxy.

The optional convertion of $C_{1-4}$ alkoxycarbonyl, phenoxycarbonyl or benzyloxycarbonyl into $R_1$ may be carried out as described hereinbefore. In fact, in relation to the most preferred process of the present invention, namely the first process involving the cyclisation of a compound of formula (II), it is preferred that any such conversion is carried out at this stage providing of course that the resulting group ($R_1$) is not likely to interfere with the course of any subsequent reaction or to be affected by it. If, however, either is likely, then it is preferred to maintain the $C_{1-4}$ alkoxycarbonyl, phenoxycarbonyl or benzyloxycarbonyl group until after the subsequent reactions have been carried out and then to carry out the required conversion. In the preferred case when, in a compound of formula (XV), G is $CH_2L_1$, $L_1$ being hydroxy, and $R_1'$ is $R_1$ and is methyl, it is particularly advantageous to prepare such compounds by reducing both ester functions in the corresponding compound of formula (XVII) in one operation. Thus, the COOR$_{11}$ ester function becomes hydroxymethyl and the COOR$_4$ ester function becomes methyl. A convenient reducing agent for such a reduction is lithium aluminium hydride, which is preferably used at room temperature or above in a solvent, such as diethyl ether.

The compound of formula (XVII) may be prepared by reacting a compound of formula (XIX);

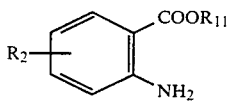

wherein R$_2$ and R$_{11}$ are as defined hereinbefore, with a compound of formula (XX);

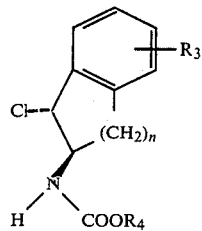

wherein R$_3$, R$_4$ and n are as defined hereinbefore.

The reaction between the compounds of formulae (XIX), when R$_2$ is hydrogen, and (XX) is preferably carried out with an excess of the compound of formula (XIX) as solvent.

Alternatively although less preferred when R$_2$ is hydrogen, the compound of formula (XV) may be prepared by reacting a compound of formula (XXI);

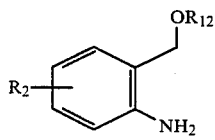

wherein R$_2$ is as defined hereinbefore and R$_{12}$ is hydrogen or C$_{1-4}$ alkyl, with a compound of formula (XX), as defined hereinbefore; in the case when R$_{12}$ is hydrogen, optionally converting the hydroxy group of the hydroxymethyl substituent in the resulting compound of formula (XVIII), as defined hereinbefore, into another leaving group (L$_1$), or optionally oxidising the hydroxymethyl substituent to formyl or carboxy and optionally esterifying a carboxy group so formed into a C$_{1-4}$ alkyl ester thereof; and optionally converting the C$_{1-4}$ alkoxycarbonyl, phenoxycarbonyl or benzyloxycarbonyl into R$_1$.

The reaction between the compounds of formulae (XXI) and (XX) is preferably carried out in a solvent, such as dimethylformamide, in the presence of barium carbonate.

The compound of formula (XX) may be prepared by reacting a compound of formula (XXII);

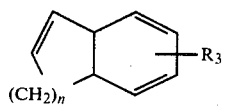

wherein R$_3$ and n are as defined hereinbefore, with a compound of formula (XXIII);

$$Cl_2NCO_2R_4 \quad (XXIII)$$

wherein R$_4$ is as defined hereinbefore.

The reaction between the compounds of formulae (XXII) and (XXIII) is preferably carried out in a solvent, such as toluene, at a temperature of 25° to 75° C.

The compound of formula (XXIII) is preferably prepared in situ by reacting a mixture of chlorine and a compound of formula (XXIV);

$$H_2NCO_2R_4 \quad (XXIV)$$

wherein R$_4$ is as defined hereinbefore.

The reaction between the compound of formula (XXIV) and chlorine is preferably carried out in buffered aqueous solution.

The compounds of formulae (XIX), (XXI), (XXII) and (XXIV) are known compounds or can be prepared in a manner similar to the preparation of known compounds.

The intermediates of formulae (II), (III), (IV), (IX), (X), (XII), (XIII), (XIV), (XV), (XVI), (XVII), and (XVIII) are novel intermediates and represent part of the present invention. Collectively they are of formulae (XXV) and (XXVI);

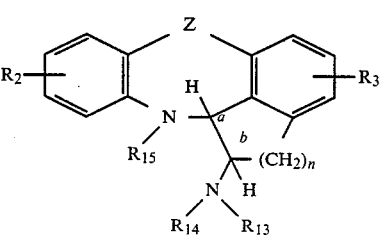

wherein R$_2$, R$_3$, n and the configuration of the C$_a$ and C$_b$ hydrogen atoms are as defined hereinbefore and either Z is methylene and either R$_{13}$ is COOR$_4$ or R$_{10}$, R$_4$ and R$_{10}$ being as defined hereinbefore, and R$_{14}$ and R$_{15}$ together are C$_{1-3}$ alklyene, or R$_{13}$ is R$_1'$, as defined hereinbefore, and R$_{14}$ and R$_{15}$ are both hydrogen, or R$_{14}$ is W, as defined hereinbefore, and R$_{15}$ is V, as defined hereinbefore, or R$_{14}$ is Y, as defined hereinbefore, and R$_{15}$ is X, as defined hereinbefore, or R$_{14}$ and R$_{15}$ together are (CO)$_{s'}$—(CH$_2$)$_{t'}$—(CO)$_{u'}$, s', t' and u' being as defined hereinbefore, or Z is J, as hereinbefore defined, R$_{13}$ is R$_1'$, as hereinbefore defined, and R$_{14}$ and R$_{15}$ together are C$_{1-3}$ alkylene; and

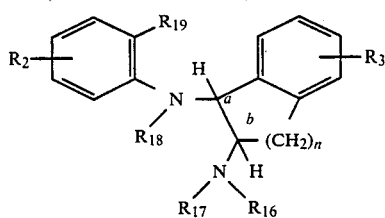

(XXVI)

wherein $R_2$, $R_3$, n and the configuration of the $C_a$ and $C_b$ hydrogen atoms are as defined hereinbefore and either $R_{16}$ is $R_1'$, as defined hereinbefore, and $R_{17}$ and $R_{18}$ are both hydrogen or together are either $C_{1-3}$ alkylene or $(CO)_{s'}$—$(CH)_{t'}$—$(CO)_{u'}$, s', t' and u' being as defined hereinbefore, and $R_{19}$ is G, as defined hereinbefore, or $R_{16}$ is $COOR_4$, $R_4$ being as defined hereinbefore, $R_{17}$ and $R_{18}$ are both hydrogen and $R_{19}$ is $COOR_{11}$, $R_{11}$ being as defined hereinfore, or hydroxymethyl.

The present invention also provides a pharmaceutical composition, which comprises a compound of formula (I), or an N-oxide or pharmaceutically acceptable salt thereof, and a pharmaceutically acceptable carrier.

A pharmaceutical composition of the invention, which may be prepared by a mixture, is usually adapted for oral or parenteral administration and, as such, may be in the form of tablets, capsules, oral liquid preparations, powders, granules, lozenges, reconstitutable powders, or injectable or infusable solutions or suspensions. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention, or an N-oxide or pharmaceutically acceptable salt theeof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. Parenteral suspensions are prepared in substantially the same manner, except that the compound is suspended in the vehicle instead of being dissolved and sterilised by exposure to ethylene oxide before suspension in a sterile vehicle. Advantageously, a surfactant or wetting agent is included in the composition to facilitate uniform distribution of the compound.

The dose of the compound used in the treatment of CNS disorders, such as depression or anxiety, will vary in the usual way with the seriousness of the disorders, the weight of the sufferer, and other similar factors. However, as a general guide suitable unit doses may be 0.05 to 10.0 mg, for example 0.2 to 1 mg; and such unit doses may be administered more than once a day, for example two or three times a day, so that the total daily dosage is in the range of about 0.01 to 10 mg/kg; and such therapy may extend for a number of weeks or months.

The invention also provides a method of treatment of CNS disorders, in particular depression in mammals including humans, which comprises administering to the sufferer an anti-depressant effective amount of a compound of the invention, or an N-oxide or pharmaceutically acceptable salt thereof.

The invention further provides a compound of the invention, or an N-oxide or pharmaceutically acceptable salt thereof, for use in the treatment of CNS disorders in particular depression.

The following Examples illustrate the preparation of the compounds of the invention. The following Descriptions illustrate the preparation of intermediates to the compounds of the present invention. All temperatures are in degrees celsius and 'Rec' means recrystalised from.

DESCRIPTION 1 trans-1-Chloro-2-ethoxycarbonylaminoindane (D1)

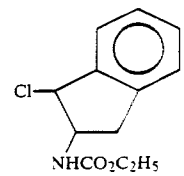

The title compound was prepared according to the procedure of B. J. Walker and P. J. Wrobel, J. C. S. Chem. Comm., 1980, 462 (85% yield; m.p. 82°-84°).

DESCRIPTION 2 trans-1-Chloro-2-ethoxycarbonylamino-1,2,3,4,-tetrahydronaphthalene (D2)

The title compound was prepared using a procedure similar to the one employed in Description 1 (74% yield; m.p. 124°-6°).

DESCRIPTION 3 trans-1-(2-Hydroxymethylanilino)-2-ethoxycarbonylamino-1,2,3,4-tetrahydronaphthalene (D3)

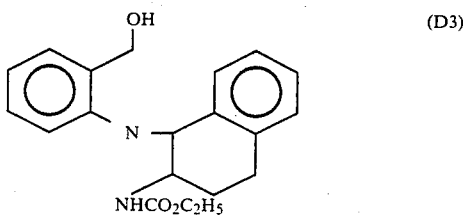

A solution of trans-1-chloro-2-ethoxycarbonylamino-1,2,3,4-tetrahydronaphthalene (12.8 g; 0.05 moles) and o-aminobenzyl alcohol (6.2 g; 0.05 moles) in dry dimethyl formamide (50 ml) was treated with finelay ground barium carbonate (5.4 g; 0.0275 moles) and stirred under nitrogen at 85° for 10 h. The reaction mixture was diluted with water and extracted into ether. The combined organic layers were washed exhaustively with water, dried ($Na_2SO_4$) and concentrated in vacuo to give a light brown foam (15.6 g) which was purified on silica gel using 25% ethyl acetate in petroleum ether 60/80 as eluant. Pooling of pure fractions produced the title compound as a colourless crystalline solid (6.1 g; 35%) m.p. 134°–5° (Rec. pentane/ether). Earlier fractions which were slightly contaminated with less polar impurity, afforded a further 1.4 g (8%) of the required product (m.p. 134°–5°) after recrystallisation from pentane/ether.

Nmr ($CDCl_3$): δ: 1.18 (3H,t,J=7), 1.5–2.5 (3H,m), 2.90 (2H,m), 4.04 (2H,q,J=7), 4.15 (1H,m), 4.57 (2H,s), 4.75 (2H, overlapping doublets), 6.65 (1H,m), 7.2 (6H,m).

DESCRIPTION 4 trans-1(2-Methoxycarbonylanilino)-2-ethoxycarbonylaminoindane (D4)

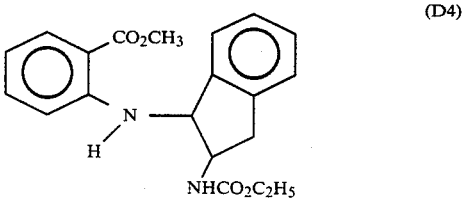

trans-1-Chloro-2-ethoxycarbonylaminoindane (20 g, 0.084 moles) was treated with methyl anthranilate (60 ml) and stirred under nitrogen at 60° for 5 hr. The resulting viscous mixture was diluted with ether (500 ml), washed exhaustively with 2.5 N HCl (8×250 ml), and then with saturated sodium bicarbonate followed by brine. After drying ($Na_2SO_4$) and concentration in vacuo a brown solid (25.7 g) was obtained. Crystallisation from pentane/ether afforded the title compound (14 g; 58%) m.p. 108°–110°. Concentration of mother liquors gave a less pure second crop (2.6 g).

Nmr ($CDCl_3$) δ: 1.21 (3H,t,J=7), 2.30 (1H,dd,J=16,6) 3.42 (1H,dd,J=16,7), 3.80 (3H,s), 3.9–4.5 (3H, m, overlapping signals), 4.92 (1H,d,J=5), 4.95 (2H, m, overlapping signals), 6.65 (1H, m), 7.26 (6H, m), 7.94 (1H,dd,J=9, 1.5).

DESCRIPTION 5 trans1-(2-Hydroxymethylanilino)-2-ethoxycarbonylaminoindane (D5)

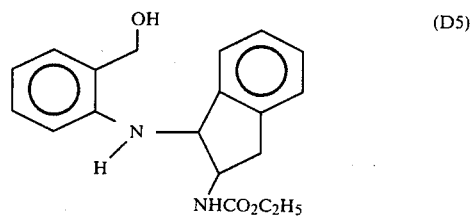

A solution of the ester D4 (1.0 g, 2.8 mmoles) in dry tetrahydrofuran (6 ml) was cooled below −10° under nitrogen and treated dropwise with Super-hydride (Lithium triethylborohydride) (10 ml of a 1 M Tetrahydroguran solution). Stirring was continued overnight at room temperature. The reaction mixture was then cooled below 0° and treated with water (1 ml) followed by 5N HCl (25 ml). After stirring for 30 mins. the mixture was diluted with pentane. The aqueous layer was washed with ether (2×20 ml) basified (40% NaOH) and extracted into ether. The organic phase was washed (brine), dried ($Na_2SO_4$) and concentrated in vacuo to give the title compound as a colourless solid (0.75 g, 81%) m.p. 115–7° (rec. ether/pentane).

Nmr ($CDCl_3$) δ: 1.17 (3H,t,J=7), 2.76 (1H,dd,J=16,8), 3.34 (1H,dd,J=16,8), 4.02 (2H,q,J=7), 4.35 (1H,m), 4.62 (2H,s), 4.82 (1H,d,J=7), 4.95 (1H,broad), 6.5–7.5 (8H,m).

DESCRIPTION 6 trans1-(4-Methoxy-2-hydroxymethylanilino)-2-ethoxycarbonylaminoindane (D6)

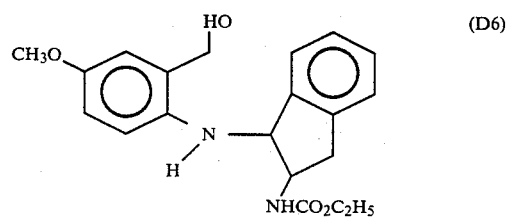

A solution of 2-amino-5-methoxybenzyl alcohol (5 g; 32.7 m. mol) and trans-1-chloro-2-ethoxycarbonylaminoindane (7.83 g; 32.7 m.mol) in dmethylformamide (80 ml) was treated with barium carbonate (3.37 g; 17 m.mol) in a manner similar to that in Description 3 to give the title compound (5.1 g; 44%), m.p. 142°–144° (from ethyl acetate).

Nmr ($CDCl_3$) δ: 1.08(3H,t,$CO_2CH_2\underline{CH}_3$); 2.40–3.45 (2H,dd,2×CH); 3.60(3H,s,$OCH_3$); 4.40(2H,s,$\underline{CH}_2OH$); 3.50–4.80(5H,m,$CO_2\underline{CH}_2$+$N\underline{HCH}$+OH); 5.47 (1H,d,8Hz;$\underline{C}H$); 6.40–7.40(7H,m,aromatic CH).

DESCRIPTION 7 trans-1-Ethoxycarbonylamino-1,2,11,11a-tetrahydro-6H-benzo[f]indeno[1,7-bc]azepine (D7)

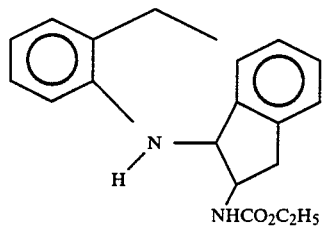

(D7)

The alcohol prepared in Description 5 (8.6 g; 0.026 moles) was dissolved in methanesulphonic acid (86 g; 58 ml) and the cooled solution was treated with phosphorus pentoxide (17.2 g) and stirred at room temperature for 4 days. The mixture was poured onto ice, neutralised to pH7 (40% NaOH) and extracted into ether. The organic layers were washed (water), dried ($Na_2SO_4$) and concentrated in vacuo to give a yellow foam (6.4 G) containing two faster running products on tlc (Rf values 0.77 and 0.6—$SiO_2$/petroleum ether/ether-3/1). The mixture was separated on silica gel using 20% ethyl acetate in petroleum ether as eluant. The more polar component corresponded to the title compound and was isolated as a colourless crystalline solid (1.87 g; 23%).

Nmr ($CDCl_3$) $\delta 1.28$ (3H,t,J=7), 2,57 (1H,dd,J=16,10), 3.15 (1H,dd,J=16,8), 3.63 (1H,d,J=15), 4,25 (5H, overlapping signals), 4.68 (1H,d,J=8), 5.07 (1H, broad doublet), 6.5–7.3 (7H,m).

DESCRIPTION 8 trans-1-Ethoxycarbonylamino-1,2,3,7,12,12a-hexahydrobenzo[f]naphth[1,8-bc]azepine (D8)

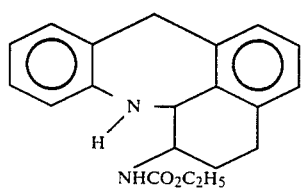

(D8)

The title compound was prepared using a procedure analogous to the one outlined in Description 7 (21% yield).

Nmr ($CDCl_3$) $\delta$: 1.25 (3H,t,J=7), 1.5–2.8 (2H,m), 2.85 (2H,m), 3.38 (1H,d,J=15), 3.75–4.90 (4H, overlapping signals), 4.85 (1H,d,J=15), 4.95 (1H,d,broad), 5.07 (1H,d,J=6), 6.35–7.4 (7H,m).

DESCRIPTION 9 trans-1-Ethoxycarbonylamino-11-bromoacetyl-1,2,11,11a-tetrahydro-6H-benzo[f]indeno[1,7-bc]azepine (D9)

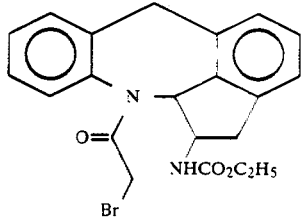

(D9)

Bromoacetyl bromide (0.88 ml; 0.01 moles) was added dropwise to a solution of the amine prepared in Description 7 (3.08 g; 0.01 moles) in dry methylene chloride (25 ml) containing finely ground potassium carbonate (2.76 g; 0.02 moles) and cooled to 0°. Stirring was continued for 27 hours and during this period a further portion (0.2 ml) of bromoacetyl bromide was added. The mixture was then treated with water and after separation of the organic phase the aqueous layer was extracted with methylene chloride. The combined organic layers were washed (water), dried, ($Na_2SO_4$) and concentrated in vacuo to give a yellow solid. Purification by trituration with pentane/ether afforded the title compound as a colourless crystalline solid (4.1 g; 95%) m.p. 207.5°–210° C. (rec. ether).

Nmr ($CDCl_3$) $\delta 1.33$ (3H,t,J=7), 2.75 (1H,dd,H=15,10), 3.32 (1H,dd,J=16,8), 3.44 (1H,d,J=13), 3.80 (2H,s), 4.2 (4H,overlapping signals), 6.1 (2H,overlapping doublets) 6.8–7.5 (7H,m).

DESCRIPTION 10 trans-1-Ethoxycarbonylamino-12-bromoacetyl-1,2,3,7,12,12a-hexahydrobenzo[f]napth[1,8-bc]azepine (D10)

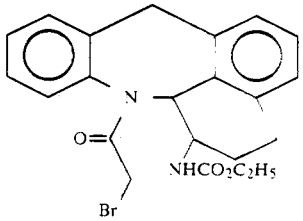

(D10)

The title compound was prepared using a procedure similar to the one outlined in Description 9 (77% yield).

Nmr ($CDCl_3$) $\delta$: 1,30 (3H,t,J=7), 2.0 (2H,m), 2.80 (2H,m), 3,44 (1H,d,J=14), 3,65 (1H,d,J=10), 3.72 (1H,d,J=10), 3,89 (1H,m), 4.19 (2H,q,J=7), 4.53 (1H,d,J=14), 5,54 (1H,d,J=9), 5,97 (1H,d,J=10), 6.97 (3H,m), 7,30 (4H,m).

DESCRIPTION 11 trans-10-Oxo-1,10,11,12,12a,12b-Hexahydro-5H-9b,12-diazobenzo[5,6]cyclohepta[1,2,3,4-def]fluorene-12-carboxylic acid ether ester (D11)

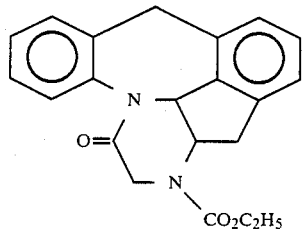

(D11)

A solution of the urethane prepared in Description 9 (3.35 g; 7.8 mmoles) in dry dimethyl formamide (200 ml) was added over a period of 30 minutes to a stirred suspension of sodium hydride (0.26 g of 80% dispersion in oil; 8.6 mmoles) in the same dry solvent (20 ml) under nitrogen. Reaction temperature was maintained below 5° during addition and then allowed to rise to room temperature while stirring was continued for a further 3h. The mixture was then carefully diluted with water and extracted into ether. The organic phase was washed exhaustively with water, dried ($Na_2SO_4$) and concentrated to give the title compound as a pale yellow solid (2.35 g; 90%) which was used without further purification.

Nmr ($CDCl_3$) δ: 1.35 (3H,t,J=7), 2.75 (1H,dd,J=16,10), 3,50 (1H,d,J=14), 3.55 (1H,dd,overlapping), 3.65–4.50 (4H,overlapping signals), 4.86 (1H,d,J=16), 5.35 (1H,d,J=11), 6.80–7.40 (6H,m), 7.60 (1H,m).

DESCRIPTION 12 trans-11-Oxo-1,2,6,11,12,13,13a,13b-octahydro-10b,13-diazabenzo[gh]pleiadene-13-carboxylic acid ethyl ester (D12)

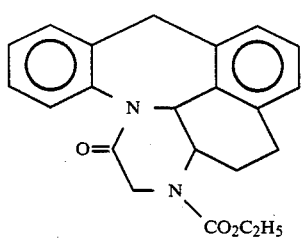

(D12)

The title compound was prepared using the method outlined in Description 11 (yield 75%).

Nmr ($CDCl_3$) δ: 1.35 (3H,t,J=7), 2.85 (3H,m), 3.50 (2H,m), 3.80–4.50 (5H,overlapping signals), 4.95 (1H,d,J=16), 5.33(1H,d,J=11), 6.80–7.40 (7H,m).

DESCRIPTION 13 trans-1,10,11,12,12a,12b-Hexahydro-5H-9b,12-diazabenzo[5,6]cyclohepta[1,2,3,4-def]fluorene-12-carboxylic acid ethyl ester (D13)

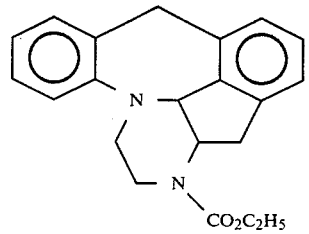

(D13)

A solution of the urethane prepared in Description 11 (2.2 g; 6.3 mmoles) in dry tetrahydrofuran (15 ml) was added dropwise to 10.5 ml of 1 M diborane in tetrahydrofuran cooled to ice temperature under nitrogen. The solution was then refluxed for 2 hours. After cooling to −10° the mixture was carefully acidified (5 N HCl) and stirred for 30 mins. Solvent was removed in vacuo and the residue treated with 2N NaOH before extraction into ether. The dried ($Na_2SO_4$) organic phase was concentrated in vacuo to give a foam (1.9 g). Purification on silica gel using 15% ethyl acetate in petroleum ether 60/80 as eluant afforded the title compound as a colourless foam (1.45 g; 70%).

Nmr ($CDCl_3$) δ: 1.32 (3H,t,J=7), 3.0–4.7 12H,m), 6.6–7.3 '7H,m).

DESCRIPTION 14 trans-1,2,6,11,12,13,13a,13b-Octahydro-10b,13-diazabenzo[gh]pleiadene-13-carboxylic acid ethyl ester (D14)

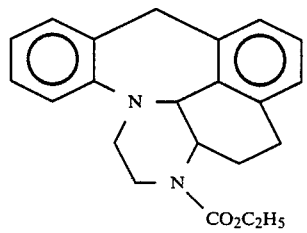

(D14)

The title compound was prepared using a method similar to the one outlined in Description 13.

Nmr ($CDCl_3$) δ: 1.20 (3H,t,J=7), 1.50–2.50 (2H,m), 2.75 2H,m), 3.25–4,40 (9H,m,overlapping signals), 4.52 (1H,d,J=13), 7.0 (7H,m).

DESCRIPTION 15 trans-1-(4-Methoxy-2-hydroxymethylanilino)-2-methylaminoindane (D15)

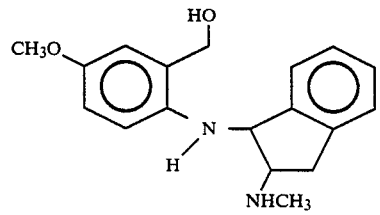

(D15)

A solution of the carbamate prepared in Description 6 (4.00 g; 11.23 m.mol) in dry tetrahydrofuran (20 ml) was added dropwise to a stirred suspension of lithium aluminium hydride (1.0 g; 26.3 m.mol) in dry ether (10 ml), under a nitrogen atmosphere, at 0°. The mixture was allowed to warm to room temperature and stirring continued for 2 days. The excess of hydride was decomposed as described in Example Ia and work-up gave a brown gum (2.66 g). Chromatography on Kieselgel 60 (100 g) in ethyl acetate containing increasing amounts of methanol gave the title compound as a pale gum (1.086 g; 33%).

Nmr (CDCl$_3$) δ: 2.37(3H,s,NCH$_3$); 2.50–3.90 (6H,br,CH$_2$+CH+2×NH+OH); 3.64 (3H,s,OCH$_3$); 4.47(2H,s,CH$_2$OH); 4.50–4.78(1H,d,CH); 6.54–6.85 and 7.05–7.30 (7H,m,aromatic CH).

DESCRIPTION 16 trans-4-(4-Methoxy-2-hydroxymethylphenyl)-1-methyl2,3,4,4a,9,9a-hexahydro-1H-indeno[1,2-b]pyrazine (D16)

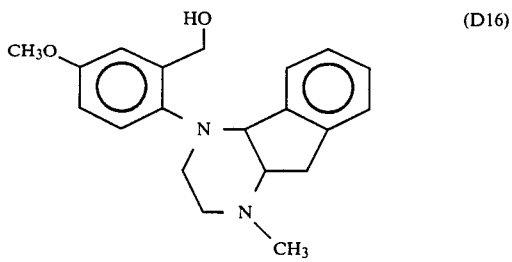

A solution of the diamine prepared in Description 15 (880 mg; 2.95 m.mol) and dry triethylamine (2 ml) in dibromoethane (6 ml) was added dropwise, over 30 min, to dibromoethane (10 ml) at 100° with stirring, under a nitrogen atmosphere. After 1hr, triethylamine (2 ml) was added and stirring continued for a further 1hr at 100°. The mixture was allowed to cool to room temperature and then partitioned between dilute sodium hydroxide (200 ml) and chloroform (200 ml). The organic phase was washed with water (2×100 ml), saturated brine (50 ml) and dried (K$_2$CO$_3$). Evaporation in vacuo gave a buff solid (0.8 g) wich was recrystallised from chloroformether to give the title compound as off-white crystals (478 mg; 50%), m.p. 179°–183°.

Nmr (CDCl$_3$): δ: 2.35–3.25 (8H,m,3×CH$_2$+CH+OH), 2.40 (3H,s,NCH$_3$), 3.83(3H,s,OCH$_3$), 4.20(1H,d J9Hz,CH), 4.50–5.00 (2H,ABq, J13Hz,CH$_2$OH), 6.15 (1H,dJ8Hz,CH), 6.75–7.45 (6H,m,aromatic).

DESCRIPTION 17 trans-1-(2-Hydroxymethylanilino)-2-methylaminoindane (D17)

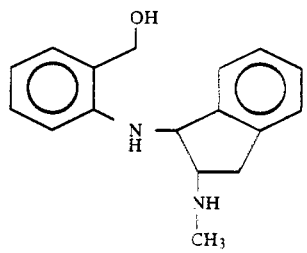

A solution of trans 1-(2-methoxycarbonylanilino)-2-ethoxycarbonylaminoindane (1.73 kg; 4.9 moles) in diethyl ether (36 l) was added dropwise to a suspension of lithium aluminium hydride (900 g; 23.7 moles) in diethyl ether (28 l), under nitrogen, over a period of ca 1.5 h. After stirring overnight at room temperature the excess lithium aluminium hydride was carefully decomposed with water (2.5 l), and 10% sodium hydroxide (30 l) and water (5 l) was added. The organic layer was separated and the aqueous phase extracted with two further portions of ether (2×20 l). The combined extracts were washed (water), dried (MgSO$_4$) and concentrated. Crystallisation from ethyl acetate/pet. ether afforded the title compound (1.17 Kg; 89%) m.p. 113°–4°.

Nmr (CDCl$_3$) δ: 2.2 (2H, brs, exchanges with D$_2$O), 2.45 (3H,s), 2.5–3.5 (3H,overlapping signals), 4.6 (2H,s), 4.8 (1H, t, J=8), 5.07 (1H, d, J=8, exchanges with D$_2$O),6.5–7.5 (8H,m).

DESCRIPTION 18 trans-4-(5-Chloro-2-hydroxymethylphenyl)-1-methyl-2,3,4,4a,9,9a-hexahydro-1H-indeno[1,2-b]pyrazine (D18)

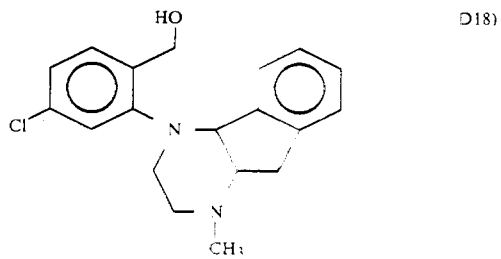

The title compound was prepared in a manner similar to that in Description 16.

Nmr (CDCl$_3$) δ: 2.35 (3H,s,NCH$_3$), 2.40–3.40 (7H, overlapping signals), 4.18 (1H,d,J9 Hz), 4.40–5.00 (2H, ABq, J13 Hz, CH$_2$OH) 6.10 (1H,d,J7 Hz, aromatic CH) 6.60–7.40 (6H,m,aromatic CH).

DESCRIPTION 19 trans-4-(2-Hydroxymethyl-4-methylphenyl)-1-methyl-2,3,4,4a,9,9a-hexahydro-1H-indeno[1,2-b]pyrazine (D19)

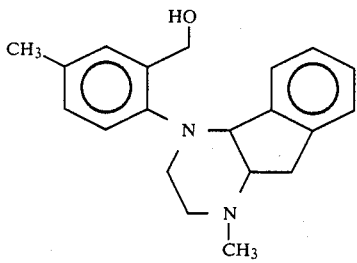

The title compound was prepared in a manner similar to that in Description 16.

Nmr (CDCl₃) δ: 2.34 and 2.38 (2×3H,s, 2×CH₃), 2.30–3.25 (7H,overlapping signals), 4.17 (1H,d,J9 Hz, CH), 4.25–5.20 (3H,m,CH₂OH), 6.10 (1H,d,J7 Hz, aromatic CH), 6.53–7.25 (6H,m, aromatic CH).

DESCRIPTION 20 trans-4-(2-Hydroxymethylphenyl)-1-methyl-2,3,4,4a,9,9a-hexahydro-1H-indeno[1,2-b]pyrazine (D20)

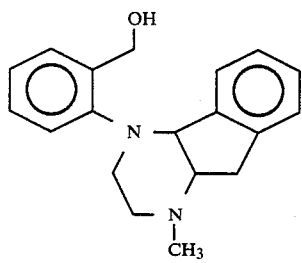

A solution of trans 1-(2-hydroxymethylanilino)-2-methylaminoindane (1.16 kg; 4.3 moles) in 1,2-dibromoethane (7 l, 17.1 moles) and triethylamine (2.5 l; 34 moles) was added dropwise to stirred 1,2-dibromoethane (13 l; 31.9 moles) at ca. 100° over a period of 1.5h. This was followed by triethylamine (2.5 l; 34 moles) added dropwise over 30 min. The reaction was cooled to 50° and diethyl ether (80 l) was added with good stirring. After stirring for 1 h the precipitated triethylammonium bromide was filtered off and the resulting solution concentrated in vacuo to ca 3.5 l. Addition of ethyl acetate (2.5 l) assisted crystallisation of the required product. Filtration and trituration (pet. ether) afforded the title compound as a white crystalline solid (687 g; 54%) m.p. 166°–7°.

Nmr (CDCl₃) δ: 2.3–3.4 (10H, overlapping signals), 4.3 (1H,d,J=9), 4.62 (1H,d,J=13), 4.9 (1H,brs, exchange with D₂O), 5.0 (1H,d,J=13), 6.15 (1H,d,J=8), 6.7–7.6(7H,m).

DESCRIPTION 21 trans-1-Methylamino-1,2,11,11a-tetrahydro-6H-benzo[f]indeno[1,7-bc]azepine (D21)

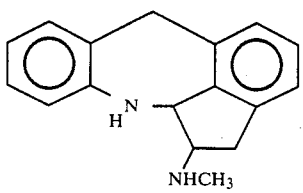

A solution of the product of Description 7 (1.16 g; 3.76 mmoles) in dry tetrahydrofuran (20 ml) was added to a stirred suspension of lithium aluminium hydride (0.42 g; 11.0 mmoles) in the same dry solvent (20 ml) under nitrogen. The mixture was refluxed for 1 h. After treatment with wet ether followed by careful addition of water the precipitate was filtered off and the filtrate concentrated to give the title compound as a dark oil (0.80 g; 85%). Maleate salt m.p. 182°-4° (Rec. acetone/ether).

Nmr (CDCl₃) δ: 2.2–2.7 (2H, m, overlapping signals), 2.6 (3H, s), 3.0–3.5 (2H, m), 3.75 (1H, d, J=16), 4.3 (1H, d, J=16), 4.50 (1H, d, J=9), 6.6–7.3 (7H, m).

DESCRIPTION 22 trans-1-Methylamino-1,2,3,7,12,12a-hexahydrobenzo[f]naphth[1,8-bc]azepine (D22)

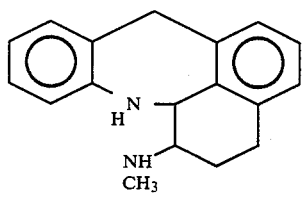

A solution of the product of Description 8 (644 mg; 2.0 mmoles) in dry dimethylformamide (4 ml) was added dropwise to a suspension of sodium hydride (66 mg of an 80% dispersion in oil; 2.2 mmoles) in the same dry solvent (1 ml) cooled to 0° under nitrogen. After 12 min methyl iodide (0.14 ml; 2.2 mmoles) was added and the mixture was stirred for a further 30 min. The reaction was then diluted with water and extracted into ether. The organic phase was washed exhaustively with water, dried (Na₂SO₄) and concentrated to give trans-1-(N-ethoxycarbonyl-N-methylamino)-1,2,3,7,12,12a-hexahydrobenzo[f] napth [1,8-bc] azepine as a yellow foam (0.64 g; 96%). A solution of this product (0.57 g; 1.7 mmoles) in ethanol (25 ml) was treated with sodium hydroxide (8 ml of a 40% aqueous solution) and the mixture refluxed under nitrogen for 26 h. Solvent was removed in vacuo and the residue was diluted with water and extracted into ether. Further purification by extraction into 2N HCl followed by neutralisation and back extractions into ether afforded the title compound as a yellow gum (0.30 g; 67%) which crystallised on standing.

Nmr (CDCl₃) δ: 1.5–2.8 (2H,m), 2.55 (3H,s), 2.75 (5H,m), 3.40 (1H,d,J=15), 4.82 (1H,d,J=15), 4.96 (1H,d,J=5), 6.3–7.3 (7H,m). Treatment with D₂O re-

EXAMPLE I trans-12-Methyl-1,10,11,12,12a,12b-hexahydro-5H-9b,12-diazabenzo[5,6]cyclohepta[1,2,3,4-def]fluorene (EI)

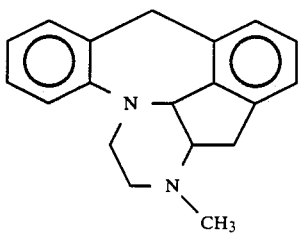

(EI)

A solution of the urethane prepared in Description 13 (1.4 g; 4.0 mmoles) in dry tetrahydrofuran (10 ml) was added dropwise to a stirred suspension of lithium aluminium hydride (0.45 g; 12.0 mmoles) in the same dry solvent (4 ml) under nitrogen, and the mixture was refluxed for 50 mins. Excess hydride was destroyed with wet ether and after careful treatment with water the precipitate of aluminium oxides was filtered off and the filtrate concentrated in vacuo to give the title compound as a light yellow foam (0.98 g; 89%) which crystallised on addition of acetone.m.p. 151°-2° (from pentane/ethyl acetate).

Nmr δ: 2.20 (1H,ddd,J=10,10,6), 2.35 (3H,s), 2.50 (1H,ddd,J=12,12,3), 2.61 (1H,dd,J=14,6), 3.45 (1H,d,J=13), 3.69 (1H,ddd,J=14.5,11,3), 3.87 (1H,ddd,J=14,3,3), 4.37 (1H,d,J=13), 4.48 (1H,d,J=10), 6.7-7.3 (7H,m).

Treatment of the free base with 1 equivalent of maleic acid in acetone solution afforded the maleate salt. m.p. 183°-5° (from acetone/ether).

|  | C | H | N |
|---|---|---|---|
| Found | 70.32 | 6.25 | 7.01 |
| $C_{23}H_{24}N_2O_4$ Requires | 70.39 | 6.16 | 7.14 |

EXAMPLE I
(Alternative Procedure)

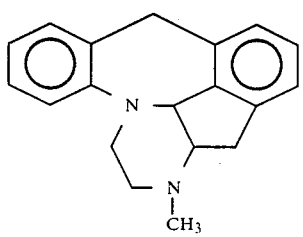

(EI)

trans-4-(2-Hydroxymethylphenyl)-1-methyl-2,3,4,4a,9,9a-hexahydro-1H-indeno[1,2-b]pyrazine (680 g; 2.31 moles) was added to stirring orthophosphoric acid (6.8 l of an 88% solution) at ca 90°. After 1 h the mixture was poured onto a mixture of ice (20 kg) and chloroform (12.5 l) and stirred vigorously as 40% sodium hydroxide solution was carefully added to neutralise the acid while the temperature was maintained below 45°. The organic layer was separated and the aqueous phase extracted with two further portions of chloroform. The combined chloroform layers were washed (water, dried (MgSO4) and concentrated in vacuo. Purification by flash chromatography, using pet. ether/acetone (70/30) as eluant, followed by crystallisation afforded the title compound as a colourless solid (560 g; 88%). m.p. 151°-2° (Rec twice pentane/ethyl acetate).

|  | C | H | N |
|---|---|---|---|
| Found | 82.43 | 7.27 | 10.30 |
| $C_{19}H_{20}N_2$ Requires | 82.57 | 7.29 | 10.13 |

EXAMPLE II trans-13-methyl-1,2,6,11,12,13,13a,13b-octahydro-10b13-diazabenzo[gh]pleiadene (EII)

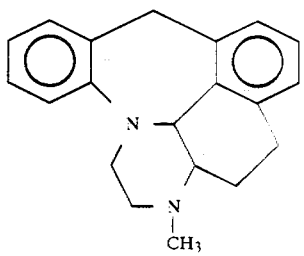

(EII)

Title compound was prepared from the urethane of Description 14 in a manner analogous to the procedure outlined in Example 1a.

Nmr (CDCl3) δ: 1.50-4.0 (14H overlapping signals) 4.90 (1H,d,J=13), 7.1 (7H,m).

Maleate Salt—m.p. 116°-7°.

|  | C | H | N |
|---|---|---|---|
| Found | 70.49 | 6.45 | 5.72 |
| $C_{24}H_{26}N_2O_4$ Requires: | 70.92 | 6.45 | 6.89 |

EXAMPLE III trans-7-Methoxy-12-methyl-1,10,11,12,12a,12b-hexahydro-5H-9b,12-diazobenzo[5,6]cyclohepta[1,2,3,4-def]-fluorene (EIII)

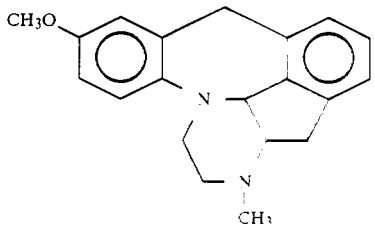

(EIII)

The alcohol prepared in Description 16 (450 mg; 1.39 m.mol) in orthophosphoric acid (6 ml) was stirred at 95° for 8 h and then allowed to cool to room temperature. The mixture was poured into water (200 ml), basified with 40% sodium hydroxide solution and extracted with chloroform (2×150 ml). The combined extracts were dried (K2CO3) and evaporation in vacuo gave a brown gum. Chromatography on Kieselgel 60 (10 g) in 10% methanol-ethyl acetate gave the title compound as a gum (2.76 mg, 65%), which solidified on standing.

Nmr (CDCl₃) δ: 2.36 (3H,s,NCH₃), 3.45(1H,d,J13 Hz, bridgehead CH), 3.74 (3H,s,OCH₃), 4.33 (1H,d,J13 Hz, bridgehead CH).

A portion (250 mg) of the above was converted into a monomaleate salt (200 mg), m.p. 208.5°–210° (from methanolether).

|  | C | H | N |
|---|---|---|---|
| Found: | 68.03 | 6.16 | 6.70 |
| C₂₄H₂₆N₂O₅ Requires: | 68.23 | 6.20 | 6.63 |

EXAMPLE IV trans-7,12-Dimethyl-1,10,11,12,12a,12b-hexahydro-5H-9b,12-diazabenzo[5,6]cyclohepta[1,2,3,4-def]fluorene (EIV)

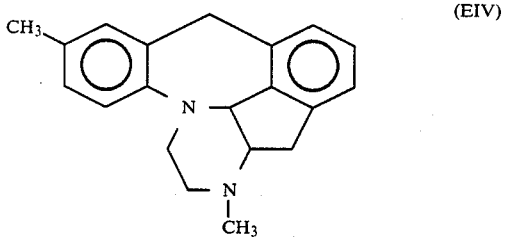

(EIV)

The title compound was prepared from the alcohol of Description 19 in a similar manner to Example III and converted into a maleate salt m.p. 207°–211° (dec) (from acetone).

|  | C | H | N |
|---|---|---|---|
| Found | 70.45 | 6.32 | 6.84 |
| C₂₄H₂₆N₂O₄ Requires: | 70.92 | 6.45 | 6.89 |

Nmr (d₆DMSO) δ: 2.18 (3H,s,CH₃), 2.85 (3H,s,NCH₃), 6.97 and 7.15 (2×3H,s,aromatic CH).

EXAMPLE V trans-8-Chloro-12-methyl-1,10,11,12,12a,12b-hexahydro-5H-9b,12-diazabenzo[5,6]cyclohepta[1,2,3,4-def]-fluorene (EV)

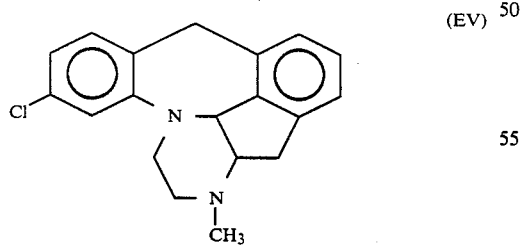

(EV)

The title compound was prepared from the alcohol of Description 18 in a similar manner to Example III.

Nmr (CDCl₃) δ: 2.30–3.10 (6H, overlapping signals), 2.34 (3H,s,NCH₃), 3.37 (1H,d,J14 Hz, bridgehead CH), 3.53–3.85 (1H,m,CH), 4.26 (1H,d,J14 Hz, bridgehead CH), 4.45 (1H,d,J9 Hz,CH), 6.50–7.15 (6H,m,aromatic CH).

Found M⁺: 310.1242. C₁₉H₁₉N₂Cl requires 310.1237.

A portion of the title compound was converted into a maleate salt, m.p. 195°–197° (from acetone).

EXAMPLE VI trans-7-Hydroxy-12-methyl-1,10,11,12,12a,12b-hexahydro-5H-9b,12-diazabenzo[5,6]cyclohepta[1,2,3,4-def]-fluorene (EVI)

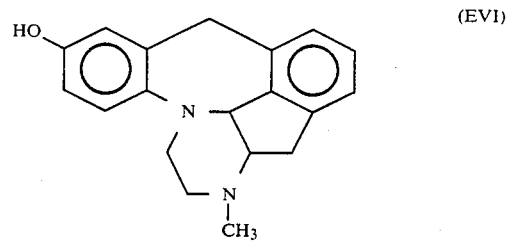

(EVI)

A solution of the methoxy compound prepared in Example III (10 mg; 0.033 mmoles) in 47% aqueous hydrobromic acid (1 ml) was heated under reflux for 5 hr and then allowed to cool to room temperature. The mixture was diluted with water (20 ml), made basic (pH about 14) with 40% sodium hydroxide solution and extracted with chloroform. The pH of the aqueous layer was adjusted to 7 with conc. hydrochloric acid and extraction with chloroform (2×20 ml) removed the product. The extracts were dried (MgSO₄) and evaporation in vacuo gave a brown gum which was fractionated by preparative layer chrmoatography on silica using 10% methanol-ethyl acetate to develop the plates. The band at Rf 0.47 afforded the title compound as a pale yellow gum (3 mg; 32%) which solidifed on standing.

Nmr (CDCl₃) δ: 2.00–3.00 (6H,m,(CH₂)₂+CH+OH); 2.35 (3H,s,NCH₃); 3.43(1H,d,J14 Hz,CH bridgehead); 3.55–3.80(2H,m,CH₂); 4.15–4.45(2H,m,CH bridgehead+NCH); 6.55–7.15 (6H,m, aromatic)

Found M⁺ 292.1572. C₁₉H₂₀N₂O requires 292.1576.

EXAMPLE VII trans-1,10,11,12,12a,12b-Hexahydro-5H-9b,12-diazabenzo [5,6]cyclohepta[1,2,3,4-def]fluorene (EVII)

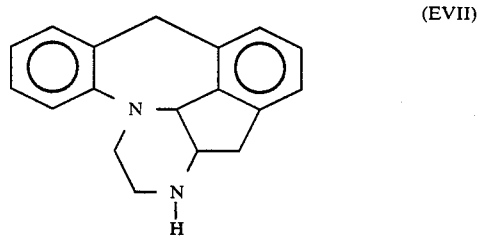

(EVII)

The product obtained in Example I (13.8 g; 0.05 moles) in dry toluene (150 ml) was treated with ethyl chloroformate (48 ml, 0.50 moles) and the mixture refluxed for 7 h. After concentration in vacuo excess reagent was removed by azeotropic distillation with several portions of toluene. The residue was partitioned between water and ether, and the aqueous layer extracted with two further portions of ether. The combined organic layers were washed (brine), dried (Na₂SO₄) and concentrated to give a crude foam (17 g) containing the required trans-1,10,11,12,12a,12b-hexahydro-5H-9b,12-diazabenzo[5,6]cyclohepta[1,2,3,4-def] fluorene-12-carboxylic acid ethyl ester. A solution of this product in ethanol (300 ml) was treated with sodium hydroxide (50 ml of a 40% aqueous solution) and refluxed under nitrogen for 6 h. After concentration in vacuo the reactioon mixture was diluted with water and extracted into ether. The organic phase was washed (brine), dried (Na₂SO₄) and concentrated to a dark foam. Chromatographic separation on silica using 30% methanol in ethyl acetate as eluant afforded the title compound as an off-white solid (3.8 g; 30%) m.p. 132.5°–135° (Rec. ethyl acetate/petroleum ether 60/80).

Nmr (CDCl₃) δ: 2.5–4.0 (9H,m,overlapping signals), 4.32 (1H,d,J=13), 4.39 (1H,d,J=10), 6.6–7.3 (7H,m).

|  | C | H | N |
| --- | --- | --- | --- |
| Found | 82.38 | 6.92 | 10.53 |
| C₁₈H₁₈N₂ Requires | 82.41 | 6.92 | 10.67 |

EXAMPLE VIII trans-12-Benzyl-1,10,11,12,12a,12b-hexahydro-5H-9b,12-diazabenzo[5,6]cyclohepta[1,2,3,4-def]fluorene (EVIII)

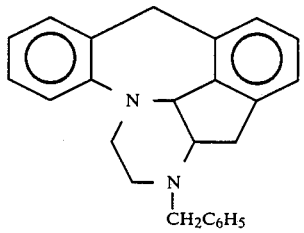
(EVIII)

A solution of the product of Example VII (500 mg; 1.9 m moles) in acetone (25 ml) containing benzyl bromide (0.25 ml; 2.1 m moles) and potassium carbonate (290 mg; 2.1 m moles) was stirred at room temperature for 6h. After concentration in vacuo the residue was treated with water and extracted into ether. The organic phase was washed (brine), dried (Na₂SO₄) and concentrated. Purification on silica gel using ethyl acetate as eluant afforded the title compound as a colourless solid (0.55 g; 82%).

Nmr (CDCl₃) δ: 2.1–3.0 (5H,m,overlapping signals), 3.16 (1H, d, J=13), 3.45 (1H, d, J=13), 3.7 (2H, m, overlapping signals), 4.0 (1H, d, J=13), 4.2–4.65 (2H, overlapping doublets), 6.6–7.6 (12H,m).

Treatment of the free base with one equivalent of maleic acid in acetone solution afforded the maleate salt. m.p. 212°–5° (dec) (Rec. acetone).

EXAMPLE IX trans-12-(Prop-2-enyl)-1,10,11,12,12a,12b-hexahydro-5H-9b,12-diaza-benzo[5,6]cyclohepta[1,2,3,4-def]fluorene (EIX)

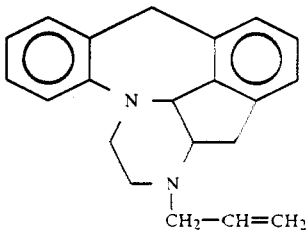
EIX)

The title compound was prepared by treatment of trans-1,10,11,12,12a,12b-hexahydro-5H-9b,12-diazabenzo[5,6]cyclohepta[1,2,3,4-def]fluorene with allyl bromide using a procedure similar to the one outlined in Example VIII. Maleate salt m.p. 187°–190° (dec).

Nmr (CDCl₃) δ: 2.1–3.1 (6H,m), 3.45 (1H,d,J=13), 3.55–3.90 (3H,m), 4.4 (1H,d,J=13), 4.5 (1H,d,J=9), 5.25–5.35 (2H,m), 5.75–6.25 (1H,m), 6.65–7.35 (7H,m).

EXAMPLE X trans-12-(Prop-2-ynyl)-1,10,11,12,12a,12b-hexahydro-5H-9b,12-diazabenzo[5,6]cyclohepta[1,2,3,4-def]fluorene (EX)

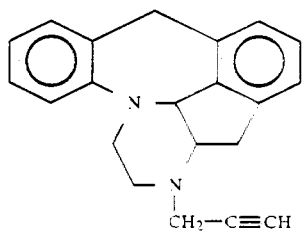
EX)

The title compound was prepared by treatment of trans-1,10,11,12,12a,12b-hexahydro-5H-9b,12-diazabenzo[5,6]cyclohepta[1,2,3,4-def] fluorene with propargyl bromide using a procedure similar to one outlined in Example VIII. Maleate salt m.p. 165°–70°.

Nmr (CDCl₃) δ:2.0–2.95 (6H,m), 3.35–3.90 (5H,m), 4.35 (1H,d,J=14), 4.50 (1H,d,J=8), 6.65–7.25 (7H,m).

EXAMPLE XI trans-12-(2-Hydroxyethyl)-1,10,11,12,12a,12b-hexahydro 5H-9b,12-diazabenzo[5,6]cyclohepta[1,2,3,4-def]fluorene (EXI)

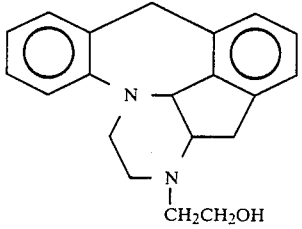

(EXI)

A solution of the product of Example VII (0.5 g; 1.90 m moles) in methanol (30 ml) containing potassium carbonate (0.26 g; 1.90 m moles) was treated with ethylene oxide as a gas for several minutes, and stirred overnight at room temperature. After concentration in vacuo, the residue was treated with water and extracted into ether. The organic phase was dried ($Na_2SO_4$) and solvent removed in vacuo. Purification on silica gel using diethyl ether as eluant, progressively incresing the polarity by adding up to 30% ethyl acetate, afforded the title compound as a cream solid (0.35 g; 60%).

Nmr ($CDCl_3$) 67 : 2.0–3.1 (8H,m), 3.45 (1H,d,J=14) 3.6–3.85 (4H,m), 4.35 (1H,d,J=14), 4.45 (1H,d,J=10), 6.7–7.4 (7H,m).

Treatment of the free base with 1 equivalent of maleic acid in acetone gave the maleate salt, m.p. 175°–7°.

| Analysis | C | H | N |
|---|---|---|---|
| Found: | 68.13 | 6.14 | 6.69 |
| $C_{20}H_{22}N_2O$ Requires: | 68.23 | 6.20 | 6.63 |

EXAMPLE XII trans-12-(2-Methoxyethyl)-1,10,11,12,12a,12b-hexahydro-5H-9b,12-diazabenzo[5,6]cyclohepta[1,2,3,4-def]-fluorene (EXII)

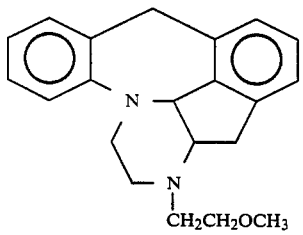

(EXII)

A solution of the product of Example VII (0.5 g; 1.90 m moles) in pyridine (3 ml) was cooled in an ice bath and treated with methoxyacetyl chloride (0.4 ml; 4.38 m moles). After stirring at room temperature for 0.5 h the reaction mixture was treated with water and extracted into ether. The organic phase was washed once with 1M hydrochloric acid, dried ($Na_2SO_4$), and concentrated in vacuo. Purification on silica gel using diethyl ether as eluant afforded the required trans-12-(methoxyacetyl)-1,10,11,12,12a,12b-hexahydro-5H-9b,12-diazabenzo[5,6]cyclohepta[1,2,3,4-def]fluorene as a brown solid (0.35 g; 55%).

A solution of this compound (0.35 g; 1.05 m moles) in dry tetrahydrofuran (15 ml) was added dropwise to a stirred suspension of lithium aluminium hydride (0.125 g; 3.2 m moles) in the same dry solvent (5 ml) under nitrogen, and the mixture was refluxed for 3h. Excess hydride was destroyed with wet ether and, after careful treatment with water, the precipitate of aluminium oxides was filtered off and the filtrate concentrated in vacuo. Purification on silica gel using 50% ethyl acetate in diethyl ether as eluant afforded the title compound as a brown oil (0.26 g; 78%).

Nmr ($CDCl_3$) δ: 2.1–3.1 (7H,m), 3.35 (3H,s), 3.45–3.95 (5H,m), 4.33 (1H,d,J=14), 4.48 (1H,d,J=10), 6.6–7.3 (7H,m).

Treatment of the free base with 1 equivalent of maleic acid in acetone solution gave the maleate salt, m.p. 170°–2°.

EXAMPLE XIII trans-12-Ethyl-1,10,11,12,12a,12b-hexahydro-5H-9b,12-diazabenzo[5,6]cyclohepta[1,2,3,4-def]fluorene (EXIII)

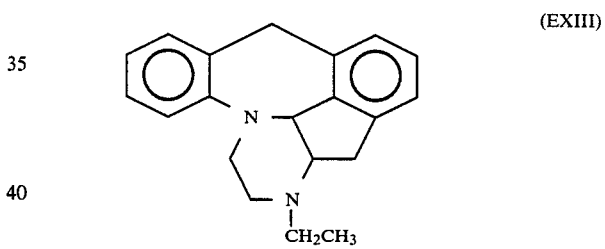

(EXIII)

A solution of the product of Example VII (0.5 g; 1.90 m moles) in dry dichloromethane (8 ml) was cooled in an ice-bath and treated with acetic anhydride (0.233 g; 2.3 m moles) in one portion. After stirring at room temperature for 0.5 h the reaction mixture was treated with water and extracted into dichloromethane. The organic phase was dried ($Na_2SO_4$) and solvent removed in vacuo. Purification on silica gel using diethyl ether as eluant afforded the required trans-12-acetyl-1,10,11,12,12a,12b-hexahydro-5H-9b,12-diazabenzo[5,6-]cyclohepta[1,2,3,4-def]fluorene as a white solid (0.54 g; 93%).

This compound was reduced according to the method of Example XII, to give the title compound and the maleate salt prepared similarly, m.p. 188°–9° (dec.).

Nmr ($CDCl_3$) δ: 1.15 (3H,t,J=8), 2.05–3.10 (7H,m,overlapping peaks), 3.45 (1H,d,J=14), 3.60–4.05 (2H,m), 4.375 (1H,d,J=14), 4.50 (1H,d,J=8), 6.65–7.35 (7H,m,overlapping peaks).

EXAMPLE XIV trans-12-Cyclohexylmethyl-1,10,11,12,12a,12b-hexahydro-5H-9b,12-diazabenzo[5,6]cyclohepta[1,2,3,4-def]-fluorene (EXIV)

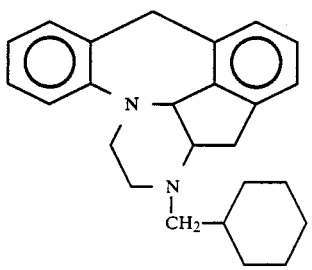
(EXIV)

The title compound was prepared according to the method of Example XII. Maleate salt m.p. 197°-9° (dec.).

Nmr (CDCl₃) δ: 0.65-3.0 (18H,m,overlapping signals), b 3.6-3.9 (3H,m), 4.3 (1H,d,J=14), 4.4 (1H,d,J=10), 6.6-7.4 (7H,m).

EXAMPLE XV trans-12-(3-Oxobutyl)-1,10,11,12,12a,12b-hexahydro-5H-9b,12-diazabenzo[5,6]cyclohepta[1,2,3,4-def]fluorene (EXV)

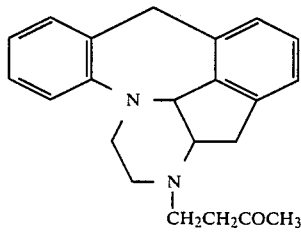
(EXV)

A solution of the product of Example VII (0.5 g; 1.90 m moles) in 1,4-dioxan (40 ml) was treated with methyl vinyl ketone (0.23 ml; 2.8 m mol) and stirred at 100° under nitrogen for 15 h. Concentration in vacuo followed by purification of the residue on silica gel using 50% ethyl acetate 60°-80° petroleum ether afforded the title compound as a beige solid (0.48 g; 76%).

Nmr (CDCl₃) δ: 2.20 (3H,s), 2.40-3.00 (9H,m,overlapping signals), 3.42 (1H,d,J=14), 3.50-3.80 (2H, m), 4.33 (1H,d,J=14), 4.44 (1H,d,J=10), 6.75-7.25 (7H,m).

Treatment of the free base with 1 equivalent of maleic acid in acetone gave the maleate salt, m.p. 148°-50°.

EXAMPLE XVI trans-12-(2-Ethoxycarbonylethyl)-1,10,11,12,12a,12b-hexahydro-5H-9b,12-diazabenzo[5,6]cyclohepta[1,2,3,4-def]fluorene (EXVI)

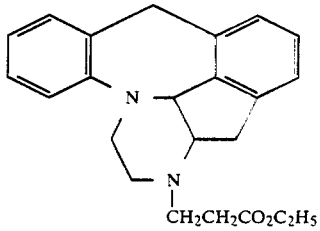
(EXVI)

The title compound was prepared from ethyl acrylate according to the method of Example XV. Maleate salt m.p. 178°-183° (dec).

Nmr (CDCl₃) δ: 1.28 (3H,t,J=8), 2.1-3.2 (9H,m,overlapping signals), 3.30-3.85 (3H,m), 3.90-4.50 (4H,m), 6.65-7.25 (7H,m).

EXAMPLE XVII trans-12-(2¹-dimethylaminoethyl)-1,10,11,12,12a,12b-hexahydro-5H-9b,12-diazabenzo[5,6]cyclohepta[1,2,3,4-def]fluorene (EXVII)

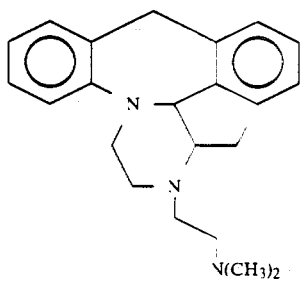
(EXVII)

A solution of the product of Example VII (0.50 g; 1.91 mmoles) in dry methylene chloride (10 ml) containing anhydrous potassium carbonate (0.29 g) was cooled in ice and treated dropwise with bromoacetyl bromide (0.183 ml; 2.1 mmoles). The reacton was allowed to warm to room temperature. After 1 h the reaction mixture was diluted with methylene chloride and washed with water. Drying (Na₂SO₄) followed by concentration in vacuo afforded trans-12-(bromoacetyl)-1,10,11,12,12a,12b-hexahydro-5H-9b,12-diazabenzo[5,6]cyclohepta[1,2,3,4-def]fluorene as a light brown foam (0.73 g). This material was dissolved in a mixture of ethanol (50 ml) and 1,4-dioxan (25 ml) and treated with dimethylamine (5 ml of 33% w/w solution in industrial methylated spirits). After 0.5 h the solvent was removed in vacuo, and trituration of the residue with ether afforded an off white solid characterised as trans-12-(dimethylaminoacetyl)-1,10,11,12,12a,12b-diazabenzo[5,6]cyclohepta[1,2,3,4-def]fluorene. Refluxing this product in dry tetrahydrofuran (100 ml) with lithium aluminium hydride (0.21 g; 5.7 mmoles) for 2 h afforded the title compound as a light brown oil (0.45 g; 70%).

Nmr (CDCl₃) δ: 2.30 (6H,s), 2.30-3.15 (9H,m,overlapping signals), 3.43 (1H,d,J=13), 3.55-3.90 (2H,m), 4.35 (1H,d,J=13), 4.50 (1H,d,J=9), 6.6-7.3 (7H,m).

PHARMACOLOGY

Compounds of the invention inhibit the behavioural symptoms induced by 5-methoxy-N,N-dimethyltryptamine (5-MDMT), a central 5-hydroxytryptamine agonist, and are central 5HT antagonists. As such they would be expected to posses antidepressant (Ogren, S.O., Fuxe, K., Agnati, L.F., Gustafsson J.A., Jonsson, G., and Holm A.C., 1979, J Neural Trans, 46, 85-103) and/or anxiolytic (Stein, L., Kline, D., and Bellugi, J.D., 1975, in Advances in Biochemical Pschopharmacology, ed Costa, E., and Greengard, P., Vol 14, 29-44, Raven Press, NY) activity.

METHOD

Mice ( ♂ CD-1 Charles River) are pretreated with the compounds (10 animals/group) under investigation and 1h later are injected with 10 mg/kg i.p. 5-methoxy-N,N-dimethyltryptamine (Sigma). The symptoms of forepaw tapping movements, head jerks and splayed limbs are scored: 1, present; 0, absent, giving a maximum score of 3/mouse or 30/group. Results are expressed as the percentage inhibition compared to the group treated with 5-methoxy-N,N-dimethyltryptamine alone. The dose of compound inhibiting the symptoms by 50% is determined graphically. The results are shown in Table 1.

TOXICITY

No toxic effects were observed in the above tests.

TABLE 1

| Compound | ED$_{50}$ mg/kg (p.o.) |
| --- | --- |
| trans-12-Methyl-1,10,11,12,12a,12b,-hexahydro-5H—9b,12-diazabenzo[5,6]cyclohepta[1,2,3,4-def]fluorene (Example 1) | 8 |

BIOCHEMISTRY

Blockade of presynaptic $\alpha_2$-adrenoceptors on noradrenergic neurones effects an increase in intrasynaptic noradrenaline, and thus in the central nervous system could be expected to have an antidepressant effect. [$^3$H]-Clonidine binds to $\alpha_2$-adrenoceptor sites and inhibition of this binding correlates with the blockade of $\alpha_2$-adrenoceptors. In vitro inhibition by some of the present compounds of the binding of [$^3$H]-clonidine to isolated rat-brain synaptic membrane fragments was therefore determined to provide an indication of antidepressant activity. This was carried out using standard biochemical binding study techniques, by the method of Maggi et al, Eur. J. Pham. 1980, 61, 91. IC$_{50}$ values were obtained from log [dose] against % inhibition curves; Ki values were determined using the Cheng-Prusoff equation. The results are shown in Table 2.

TABLE 2

| Compound | Ki (nm) |
| --- | --- |
| trans-12-Methyl-1,10,11,12,12a,12b-hexahydro-5H—9b,12-diazabenzo[5,6]cyclohepta[1,2,3,4-def]fluorene (Example I) | 88 |
| trans-13-Methyl-1,2,6,11,12,13,13a,13b-octahydro-10b,13-diazabenzo[gh]pleiadene (Example II) | 169 |

What is claim is:

1. A compound of formula (I),

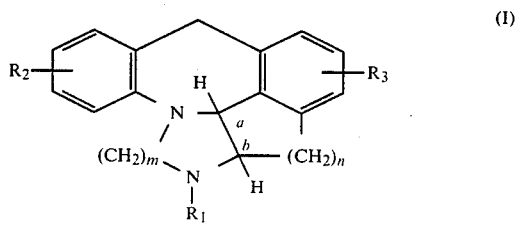

or an N-oxide or pharmaceutically acceptable salt thereof, wherein $R_1$ is hydrogen, $C_{1-7}$ alkyl, $C_{3-7}$ cycloalkyl, $C_{4-7}$ cycloalkenyl or $C_{1-4}$ alkyl substituted by $C_{2-7}$ alkenyl, $C_{2-7}$ alkynyl, $C_{3-7}$ cycloalkyl, hydroxy, thiol, $C_{1-4}$ alkoxy, $C_{1-4}$ alkylthio, carboxy, $C_{1-4}$ alkoxycarbonyl, $C_{1-4}$ alkanoyl, amino optionally substituted by one or two $C_{1-4}$ alkyls or by $C_{4-6}$ polymethylene optionally having an oxygen or nitrogen atom, aminocarbonyl optionally N-substituted by one or two $C_{1-4}$ alkyls, or benzoyl or phenyl either being optionally ring-substituted by $C_{1-4}$ alkyl, $C_{1-4}$ alkoxy, halogen or trifluoromethyl, $R_2$ and $R_3$ are the same or different and are hydrogen, hydroxy, $C_{1-4}$ alkyl, $C_{1-4}$ alkoxy, $C_{1-4}$ alkylthio, halogen or trifluoromethyl, m is 2 and n is 1 or 2, the hydrogen atom bonded to the $C_a$ carbon atom being trans to the hydrogen atom bonded to the $C_b$ carbon atom.

2. A compound according to claim 1, wherein $R_1$ is hydrogen, $C_{1-4}$ alkyl, $C_{1-4}$ alkyl substituted by amino optionally substituted by one or two $C_{1-4}$ alkyls or by $C_{4-6}$ polymethylene optionally having an oxygen or nitrogen atom, or $C_{1-4}$ alkyl substituted by phenyl optionally substituted by $C_{1-4}$ alkyl, $C_{1-4}$ alkoxy, halogen or trifluoromethyl.

3. A compound according to claim 2, wherein $R_1$ is hydrogen or $C_{1-4}$ alkyl.

4. A compound according to claim 3, wherein $R_1$ is methyl or ethyl.

5. A compound according to any one of claims 1 to 4, wherein $R_2$ and $R_3$ are the same or different and are hydrogen, $C_{1-4}$ alkyl, $C_{1-4}$ alkoxy, halogen or trifluoromethyl.

6. A compound according to claim 1, wherein $R_2$ is hydrogen, methoxy, hydroxy, methyl or chloro.

7. A compound according to claim 1, wherein $R_3$ is hydrogen.

8. A compound according to claim 1, wherein n is 1.

9. A compound which is
trans-13-methyl-1,2,6,11,12,13,13a,13b-octahydro-10b, 13-diazabenzo[gh]pleiadene;
trans-7-methoxy-12-methyl-1,10,11,12,12a,12b-hexahydro-5H-9b,12-diazabenzo[5,6]cycloahepta[1,2,3,4-def]fluorene; trans-7,12-dimethyl-1,10,11,12,12a,12b-hexahydro-5H-9b,12-diazabenzo[5,6]cyclohepta[1,2,3,4-def]fluorene;
trans-8-chloro-12-methyl-1,10,11,12,12a,12b-hexahydro-5H-9b,12-diazabenzo[5,6]cyclohepta[1,2,3,-4def]fluorene;
trans-7-hydroxy-12-methyl-1,10,11,12,12a,12b-hexahydro-5H-9b,12-diazabenzo[5,6]cyclohepta[1,2,-3,4-def]fluorene;
trans-1,10,11,12,12a,12b-hexahydro-5H-9b,12-diazabenzo[5,6]cyclohepta[1,2,3,4-def]fluorene;
trans-12-benzyl-1,10,11,12,12a,12b-hexahydro-5H-9b,12-diazabenzo[5,6]cyclohepta[1,2,3,4-def]fluorene;

trans-12-(prop-2-enyl)-1,10,11,12,12a,12b-hexahydro-5H-9b,12-diazabenzo[5,6]cyclohepta[1,2,3,4-def]fluorene;

trans-12-(prop-2-ynyl)-1,10,11,12,12a,12b-hexahydro-5H-9b,12-diazabenzo[5,6]cyclohepta[1,2,3,4-def]fluorene;

trans-12-(2-hydroxyethyl)-1,10,11,12,12a,12b-hexahydro-5H-9b,12-diazabenzo[5,6]cyclohepta[1,2,3,4-def]fluorene;

trans-12-(2-methoxyethyl)-1,10,11,12,12a,12b-hexahydro-5H-9b,12-diazabenzo[5,6]cyclohepta[1,2,3,4-def]fluorene;

trans-12-ethyl-1,10,11,12,12a,12b-hexahydro-5H-9b,12-diazabenzo[5,6]cyclohepta[1,2,3,4-def]fluorene;

trans-12-cyclohexylmethyl-1,10,11,12,12a,12b-hexahydro-5H-9b,12-diazabenzo[5,6]cyclohepta[1,2,3,4-def]fluorene;

trans-12-(3-oxobutyl)-1,10,11,12,12a,12b-hexahydro-5H-9b,12-diazabenzo[5,6]cyclohepta[1,2,3,4-def]fluorene;

trans-12-(2-ethoxycarbonylethyl)-1,10,11,12,12a,12b-hexahydro-5H-9b,12-diazabenzo[5,6]cyclohepta[1,2,3,4-def]fluorene;

trans-12-(2-dimethylaminoethyl)-1,10,11,12,12a,12b-hexahydro-5H-9b,12-diazabenzo[5,6]cyclohepta[1,2,3,4-def]fluorene;

or an N-oxide or pharmaceutically acceptable salt thereof.

10. Trans-12-methyl-1,10,11,12,12a,12b-hexahydro-5H-9b,12-diazabenzo[5,6]cyclohepta[1,2,3,4-def]fluorene, the compound prepared in Example 1a and 1b, or an N-oxide or pharmaceutically acceptable salt thereof.

11. A pharmaceutical composition, which comprises a compound of formula (I), as defined in any one of claims 1 to 10, or an N-oxide or pharmaceutically acceptable salt thereof, and a pharmaceutically acceptable carrier.

12. A method of treatment of CNS disorders, in particular depression, in mammals including humans, which comprises administering to the sufferer an antidepressant effective amount of a compound of formula (I), as defined in any one of claims 1 to 8, or an N-oxide or pharmaceutically acceptable salt thereof.

* * * * *